(12) United States Patent
Gwon

(10) Patent No.: US 12,064,663 B2
(45) Date of Patent: Aug. 20, 2024

(54) RESPIRATORY MUSCLE STRENGTHENING DEVICE

(71) Applicant: GHINNOTEK CO., LTD., Busan (KR)

(72) Inventor: Yu Hong Gwon, Busan (KR)

(73) Assignee: GHINNOTEK CO., LTD., Busan (KR)

(*) Notice: Subject to any disclaimer, the term of this patent is extended or adjusted under 35 U.S.C. 154(b) by 179 days.

(21) Appl. No.: 17/799,505

(22) PCT Filed: Sep. 1, 2021

(86) PCT No.: PCT/KR2021/011764
§ 371 (c)(1),
(2) Date: Aug. 12, 2022

(87) PCT Pub. No.: WO2022/085930
PCT Pub. Date: Apr. 28, 2022

(65) Prior Publication Data
US 2023/0347208 A1    Nov. 2, 2023

(30) Foreign Application Priority Data
Oct. 20, 2020 (KR) .................. 10-2020-0136369

(51) Int. Cl.
*A63B 23/18* (2006.01)
*A62B 23/02* (2006.01)
*A63B 24/00* (2006.01)

(52) U.S. Cl.
CPC ............. *A63B 23/18* (2013.01); *A62B 23/02* (2013.01); *A63B 24/0062* (2013.01); *A63B 2024/0065* (2013.01); *A63B 2230/42* (2013.01)

(58) Field of Classification Search
CPC ...................................................... A63B 23/18
See application file for complete search history.

(56) References Cited

U.S. PATENT DOCUMENTS 4,221,381 A * 9/1980 Ericson .................. A63B 23/18
                                                                   73/239
5,899,832 A * 5/1999 Hougen ................. A63B 23/18
                                                                   482/13
(Continued)

FOREIGN PATENT DOCUMENTS

JP          2017-532129 A      11/2017
JP          2018-528803 A      10/2018
(Continued)

OTHER PUBLICATIONS

International Search Report for PCT/KR2021/011764 mailed Feb. 7, 2022 from Korean Intellectual Property Office.

*Primary Examiner* — Andrew S Lo
(74) *Attorney, Agent, or Firm* — Paratus Law Group, PLLC

(57) ABSTRACT

A respiratory muscle strengthening device includes: a mask body which covers at least a part of the face of a user; a pressure unit which is provided at one side of the mask body to control air inhaled from the outside of the mask body; a sensor unit which is provided at one side of the mask body to measure a respiratory pattern of the user; a band part which is formed to extend from the opposite ends of the mask body and by which the mask body is brought into close contact with the face of the user; and a cover part which is detachably coupled to one side of the mask body. The cover part includes a filtering part which filters out particles in the air.

1 Claim, 28 Drawing Sheets

(56) References Cited

U.S. PATENT DOCUMENTS

| | | | | |
|---|---|---|---|---|
| 6,083,141 | A * | 7/2000 | Hougen | A61M 16/0006 |
| | | | | 128/202.16 |
| 8,590,533 | B2 * | 11/2013 | Danford | A63B 21/0004 |
| | | | | 128/206.28 |
| 9,707,444 | B1 * | 7/2017 | Danford | A63B 23/18 |
| 10,322,312 | B1 * | 6/2019 | Danford | A62B 23/025 |
| D875,237 | S * | 2/2020 | Ghazzawi | D24/110 |
| 10,780,318 | B1 * | 9/2020 | Ghazzawi | A63B 23/18 |
| 10,786,695 | B2 * | 9/2020 | Gabriel | A62B 23/025 |
| 10,953,278 | B2 * | 3/2021 | Alizoti | A61M 16/0866 |
| 11,420,095 | B2 * | 8/2022 | Aguirre, Jr. | A63H 33/00 |
| 11,439,869 | B2 * | 9/2022 | Costella | A61M 16/06 |
| D976,389 | S * | 1/2023 | Zhou | D24/110.1 |
| D1,004,767 | S * | 11/2023 | Danford | D29/108 |
| 2013/0184619 | A1 * | 7/2013 | Von Hollen | A61M 16/00 |
| | | | | 601/46 |
| 2013/0319420 | A1 * | 12/2013 | Danford | A62B 18/10 |
| | | | | 128/206.21 |
| 2016/0089553 | A1 * | 3/2016 | Dickstein | A62B 18/10 |
| | | | | 128/202.27 |
| 2016/0129286 | A1 * | 5/2016 | Danford | A62B 18/02 |
| | | | | 128/206.21 |
| 2016/0129287 | A1 * | 5/2016 | Danford | A62B 23/025 |
| | | | | 128/863 |
| 2017/0157461 | A1 * | 6/2017 | Lyapko | A63B 23/18 |
| 2023/0338775 | A1 * | 10/2023 | Rutten | A63B 21/015 |

FOREIGN PATENT DOCUMENTS

| | | |
|---|---|---|
| JP | 2019-058348 A | 4/2019 |
| KR | 10-1893251 B1 | 8/2018 |
| KR | 10-2019-0081530 A | 7/2019 |
| KR | 10-2019-0095823 A | 8/2019 |

* cited by examiner

RESPIRATORY MUSCLE STRENGTHENING DEVICE

CROSS-REFERENCE TO PRIOR APPLICATIONS

This application is a National Stage Patent Application of PCT International Patent Application No. PCT/KR2021/011764 (filed on Sep. 1, 2021) under 35 U.S.C. § 371, which claims priority to Korean Patent Application No. 10-2020-0136369 (filed on Oct. 20, 2020), which are all hereby incorporated by reference in their entirety.

BACKGROUND

The present invention relates to a respiratory muscle strengthening device and, more specifically, to a respiratory muscle strengthening device capable of performing respiration training in a pressure control type through a pressure unit, being selectively utilized for a respiratory protection if necessary, and measuring a breathing capacity of a user in real time by applying information communication technology so as to obtain data and guide respiration training based on the obtained data.

In general, a mask is a thing which covers the nose and the mouth in order to prevent viruses, dust or the likes from being inhaled into a human body or scattered into the air for health and hygiene. For instance, workers who work at hospital or in harmful working environment wear masks in order to prevent harmful materials from being inhaled into their bodies through the respiratory organs, people wear masks for keeping warm when having a cold in cold winter, or people use masks to protect themselves from yellow dust.

For example, Korean Patent No. 10-1893251 (Aug. 23, 2017) discloses a disposable mask, which is used to block fine dust. The mask includes a mask body, an ear loop which is hung on a user's ear, and a coupling body easily assembled to the mask body to connect the ear loop and the mask body with each other.

Recently, multi-purpose masks for improving cardiopulmonary endurance as well as for the above-mentioned purposes have been developed. Furthermore, it is necessary to develop a mask device for user's health in various environments and to study a health management system through improvement of cardiopulmonary endurance by using the mask device.

In addition, conventionally, a mask for covering respiratory organs, and a mask for improving cardiopulmonary endurance are provided individually. So, people need a mask that is selectively compatible as occasion demands.

SUMMARY

Accordingly, the present invention has been made in view of the above-mentioned problems occurring in the related art, and it is an object of the present invention to provide a respiratory muscle strengthening device capable of performing respiration training in a pressure control type through a pressure unit, being selectively utilized for a respiratory protection if necessary, and measuring a breathing capacity of a user in real time by applying information communication technology so as to obtain data and guide respiration training based on the obtained data.

The aspects of the present disclosure are not limited to those mentioned above, and other aspects not mentioned herein will be clearly understood by those skilled in the art from the following description.

To accomplish the above-mentioned objects, according to the present invention, there is provided a respiratory muscle strengthening device including: a mask body surrounding at least a portion of the face of a user; a pressure unit provided on one side of the mask body to control air inhaled from the outside of the mask body; a sensor unit disposed on one side of the mask body to measure a respiration pattern of the user; band units extending from both ends of the mask body so that the mask body comes into close contact with the face of the user; and a cover unit detachably coupled to one side of the mask body, wherein the cover unit comprises a filtering portion for filtering particles in the air.

Moreover, the pressure unit flows air inhaled from the outside of the mask body when a user inhales air at pressure exceeding a predetermined pressure value, and blocks the air inhaled from the outside of the mask body when the user inhales air at pressure lower than the predetermined pressure value.

Furthermore, the sensor unit includes: a communication unit for transmitting a measurement value of the sensor unit to a terminal; and an application for analyzing the user's respiration pattern on the basis of the measurement value transmitted from the communication unit.

Additionally, the sensor unit includes: a fixing portion for fixing the pressure unit and the sensor unit; and a coupling groove for coupling the fixing portion to the mask body.

In another aspect of the present invention, there is provided a respiratory muscle strengthening device including: a mouthpiece unit; a pressure unit of which one end is coupled to the mouthpiece unit to control air inhaled from the outside; and a chest wall vibration unit coupled to the other end of the pressure unit. The mouthpiece unit includes: a mouthpiece body inserted into the mouth of a user; and a mouthpiece connector of which one end is coupled to an end of the mouthpiece body and the other end surrounds at least a portion of the pressure unit to fix the pressure unit. The chest wall vibration unit includes: a chest wall vibration unit body formed in a hollow shape and having a communication hole communicating with the outside; a chest wall vibration unit connector provided at one end of the chest wall vibration unit body to fix the pressure unit by surrounding at least a portion of the pressure unit; and a vibration generator provided at the other end of the chest wall vibration unit body. The vibration generator includes: a vibrator vibrating vertically at the time of the user's exhalation; a vibrator support provided below the vibrator to prevent the vibrator from escaping downward; a cap provided at an upper portion of the vibrator to prevent the vibrator from escaping upward and having an outlet for discharging exhaled air of the user; and a silicone provided inside the chest wall vibrator body to open the communication hole when the user inhales air and to close the communication hole when the user exhales air.

In a further aspect of the present invention, there is provided a respiratory muscle strengthening device including: a mouthpiece unit; a pressure unit coupled to one side of the mouthpiece unit to control air inhaled from the outside, wherein the mouthpiece unit includes: a mouthpiece body inserted into the mouth of a user; a mouthpiece connector of which one end is coupled to an end of the mouthpiece body and the other end surrounds at least a portion of the pressure unit to fix the pressure unit; and a pressure unit cap formed to surround at least a portion of the pressure unit.

In addition, the mouthpiece unit further includes a pressure unit connector formed to surround the outer circumferential surface of the pressure unit, and the number of the pressure units is two, and the two pressure units are disposed to be axisymmetric on the basis of a central axis in the longitudinal direction of the pressure unit connector.

The respiratory muscle strengthening device according to the present invention can protect respiratory organs of a user even when the user does outdoor exercise such as jogging, riding, etc. as well as indoor exercise, and allow the user to do exercise such as jogging, riding, etc. together with the respiratory motion, thereby improving efficiency of exercise.

In addition, the respiratory muscle strengthening device according to the present invention enables a user to continuously progress the respiratory motion and measurement through an application without feeling tedium, and allows children to perform the respiratory motion and measurement with interest.

Moreover, the respiratory muscle strengthening device according to the present invention has an advantage in that components can be selectively attached or detached if necessary since being in a self-assembly type. That is, the respiratory muscle strengthening device according to the present invention has two sensor units respectively assembled at positions corresponding to the mouth and nose of the user, thereby comparing the amount of air inhaled into one among the mouth and the nose of a user and the amount of air exhaled from the other one, and more accurately measuring inhalation and exhalation of the user by measuring inhalation and exhalation of the user separately. On the other hand, the respiratory muscle strengthening device according to the present invention can be used as a mask just for protecting the respiratory organs by combining only the filter unit without coupling the sensor unit and the pressure unit.

Furthermore, the respiratory muscle strengthening device according to the present invention has two pressure units respectively assembled at positions corresponding to the mouth and nose of the user so as to separate inhalation that the air is inhaled into one of the mouth and nose of the user and exhalation that air is discharged from the other one, thereby enabling the user to select and intensively exercise a portion having a relatively small amount of respiratory capacity between inhalation and exhalation of the user since the user can perform the respiratory motion by dividing into inhalation and exhalation.

In addition, the respiratory muscle strengthening device according to the present invention has various effects of improving muscular strength and endurance of respiratory muscles, increasing the thickness of the transverse diaphragm, increasing a heart rate, increasing the maximum oxygen consumption, increasing time to be taken till exhaustion, and improving lactic acid decomposition ability.

Additionally, the respiratory muscle strengthening device according to the present invention can monitor the respiratory motion state in real time.

In addition, the respiratory muscle strengthening device according to the present invention is a threshold resistive respirator different from the conventional flow resistive respirator, thereby providing a respiratory motion effect of 35% to 40% higher than that of the conventional flow resistive device.

The advantages of the present disclosure are not limited to the above-mentioned advantages, and other advantages, which are not specifically mentioned herein, will be clearly understood by those skilled in the art from the following description.

DETAILED DESCRIPTION

The terms used herein will be briefly described, and the present invention will be described in detail.

The terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

Also, when a part "includes" or "comprises" an element, unless there is a particular description contrary thereto, the part can further include other elements, not excluding the other elements.

Hereinafter, the embodiments of the present disclosure will be described in detail with reference to accompanying drawings so that the embodiments may be easily implemented by those skilled in the art. However, the present disclosure may be implemented in various ways without being limited to the embodiments.

Specific matters of other embodiments including the technical problem, the technical solution, and the advantageous effects are included in the detailed description and drawings of the present invention. Advantages and features of the present disclosure and methods accomplishing the advantages and features will become apparent from the following detailed description of exemplary embodiments with reference to the accompanying drawings.

Hereinafter, the present invention will be described in more detail with reference to the accompanying drawings.

Figure 1:
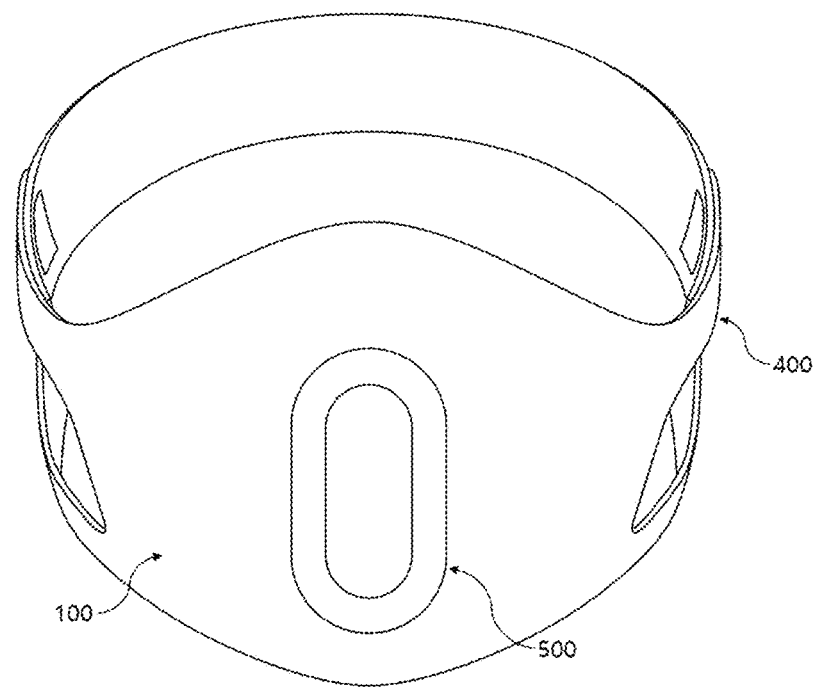
FIG. 1 is a front view of a respiratory muscle strengthening device according to an embodiment of the present invention.
Figure 2:
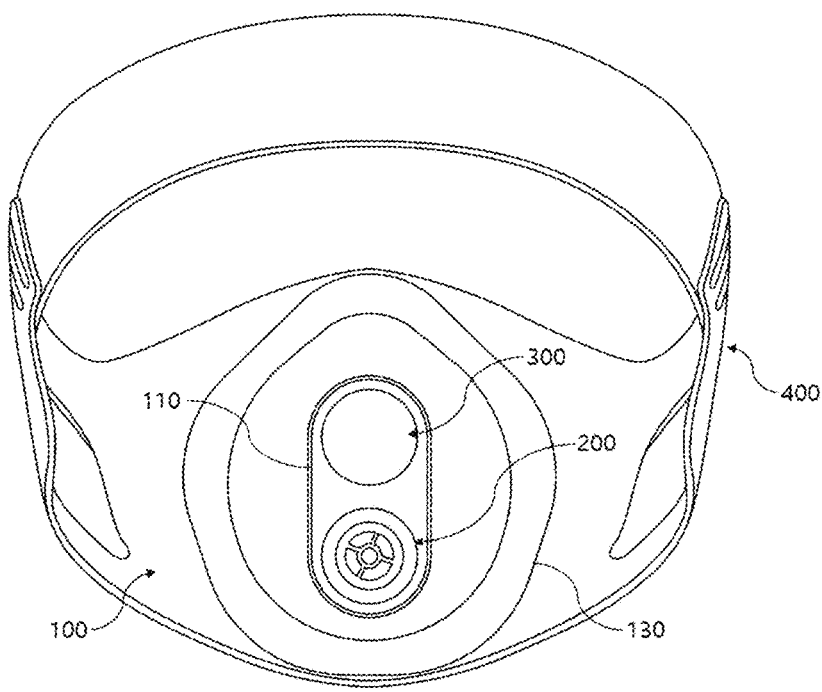
FIG. 2 is a rear view of the respiratory muscle strengthening device according to an embodiment of the present invention.
Figure 3:
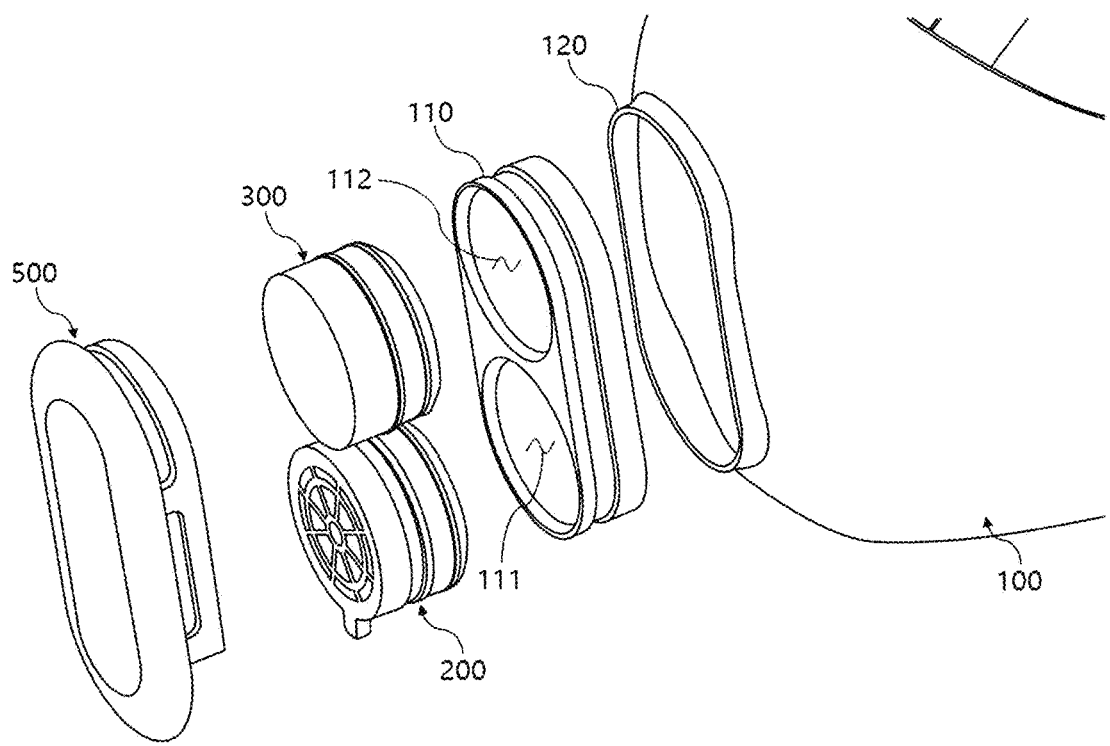
FIG. 3 is a view illustrating a configuration of the respiratory muscle strengthening device according to an embodiment of the present invention.

Referring to FIGS. 1 to 3, a respiratory muscle strengthening device according to a preferred embodiment of the present invention includes: a mask body 100 surrounding at least a portion of the face of a user; a pressure unit 200 provided on one side of the mask body 100 to control air inhaled from the outside of the mask body 100; a sensor unit 300 disposed on one side of the mask body 100 to measure a respiration pattern of the user; band units 400 formed to extend from both ends of the mask body 100 so that the mask body 100 comes into close contact with the face of the user; and a cover unit 500 detachably coupled to one side of the mask body 100.

First, the mask body 100 is provided. The mask body 100 gets in close contact with the face of the user to cover the mouth and nose of the user, thereby partitioning the inside and the outside. In this instance, the mask body 100 includes a packing 130. The packing 130 is fixed to one side of the mask body 100. Here, one side of the mask body 100 means a direction toward the face of the user from the mask body 100.

The packing 130 is inserted or interposed between the mask body 100 and the face of the user when the mask body 100 is in close contact with the face of the user. In addition, the packing 130 is made of an elastic material that is transformed into a shape corresponding to the face of the user when touching the face of the user. That is, the packing 130 is transformed to correspond to the face of the user, thereby minimizing a gap between the mask body 100 and the face of the user.

The packing 130 is detachably mounted on the mask body 100. For example, a portion of the packing 130 is inserted into the mask body 100 or is attached and fixed to the inner circumferential surface of the mask body 100. Therefore, the packing 130 can be replaced according to the body size of the user.

The mask body 100 includes a fixing portion 110 for fixing the pressure unit 200 and the sensor unit 300, and a coupling groove 120 for coupling the fixing portion 110 to the mask body 100. In this case, a plurality of coupling grooves 120 are provided in front of the mouth of the nose of the user so that the pressure unit 200 can be positioned near the nose and mouth of the user.

More specifically, the coupling groove 120 is provided on the other side of the mask body 100. Here, the other side of the mask body 100 means a direction opposed to the direction toward the face of the user from the mask body 100. The coupling groove 120 protrudes from the outer circumferential surface of the mask body 100 to the other side of the mask body 100, and functions as a frame so that the fixing portion 110 can be coupled and fixed to the mask body 100.

In addition, the fixing portion 110 is inserted and fixed into the coupling groove 120. That is, the fixing portion 110 is formed in a shape corresponding to the coupling groove 120 to be inserted and fixed into the fixing portion 110.

In this instance, the fixing portion 110 fixes the pressure unit 200 and the sensor unit 300 to be partitioned, and the pressure unit 200 is fixed at a position corresponding to the nose and the mouth of the user. More specifically, the fixing portion 110 includes a pressure unit hole 111 formed to be inserted and fixed into the pressure unit 200, and a sensor unit hole 112 formed to be spaced apart from an upper portion of the pressure unit hole 111 so that the sensor unit 300 can be inserted and fixed thereinto. Accordingly, the pressure unit 200 is inserted and fixed into the pressure unit hole 111, and the sensor unit 300 is inserted and fixed into the sensor unit hole 112.

In this instance, in a case in which the fixing portion 110 is inserted and fixed into the coupling groove 120, the pressure unit hole 111 is positioned adjacent to the respiratory organs of the user so that the pressure unit 200 is positioned adjacent to the respiratory organs of the user. Moreover, the sensor unit 300 is positioned at a predetermined distance from the upper end of the pressure unit 200 so that the user can breathe uniformly. In other words, the pressure unit 200 and the sensor unit 300 are vertically arranged in parallel, so that the user's respiration is not concentrated to any one among the pressure unit 200 and the sensor unit 300. Accordingly, the present invention can allow the user to perform the respiratory motion more accurately and can measure the respiration pattern of the user more accurately.

Alternatively, the pressure unit 200 and the sensor unit 300 have the same diameter so that the pressure unit 200 and the sensor unit 300 are exchanged with each other. For example, two pressure units 200 are provided such that the pressure units 200 are respectively inserted and fixed into the pressure unit hole 111 and the sensor unit hole 112 to focus on the respiratory motion. In this case, the pressure unit 200 positioned at a relatively higher portion among the two pressure units 200 can be focused on breathing by the nose and the pressure unit 200 positioned at a lower portion of the pressure unit 200 can be focused on breathing by the mouth. In contrast, two sensor units 300 are provided such that the sensor units 300 are respectively inserted and fixed into the pressure unit hole 111 and the sensor unit hole 112, so as to focus on measurement of a respiration pattern. In this case, the sensor unit 300 located at a relative higher portion among the two sensor units 300 measures the respiration pattern by the nose, and the sensor unit 300 positioned at a relatively lower portion measures respiration pattern by the mouth. That is, the present invention can accurately and precisely measure the respiratory motion or a respiration pattern since the pressure unit 200 and the sensor unit 300 are detachably mounted as occasion demands.

As a result, the respiratory muscle strengthening device according to the present invention can compare amounts of inhalation and exhalation of the user with each other by selectively using the two sensor units 300, and can more accurately measure inhalation and exhalation of the user by separately measuring inhalation and exhalation of the user. Furthermore, the respiratory muscle strengthening device according to the present invention enables the user to select and intensively exercise a portion having a relatively small amount of respiratory capacity between inhalation and exhalation of the user since the user can perform the respiratory motion by dividing into inhalation and exhalation when performing the respiratory motion by selectively using the two pressure units 200 as occasion demands.

Next, the pressure unit 200 is provided. The pressure unit 200 is disposed at a central portion of the other side of the mask body 100 to control air inhaled from the outside of the mask body 100. That is, the pressure unit 200 serves to control the amount of air flowing into the mask body 100 from the outside during the user's inhalation. In other words, in a case in which the pressure unit 200 is provided, the amount of air flowing into the mask body 100 from the outside decreases due to the user's inhalation.

More specifically, the pressure unit 200 flows air inhaled from the outside of the mask body 100 when inhalation is performed at pressure exceeding a predetermined pressure value, and blocks air inhaled from the outside of the mask body 100 when inhalation is performed at pressure lower than the predetermined pressure value.

Figure 4:
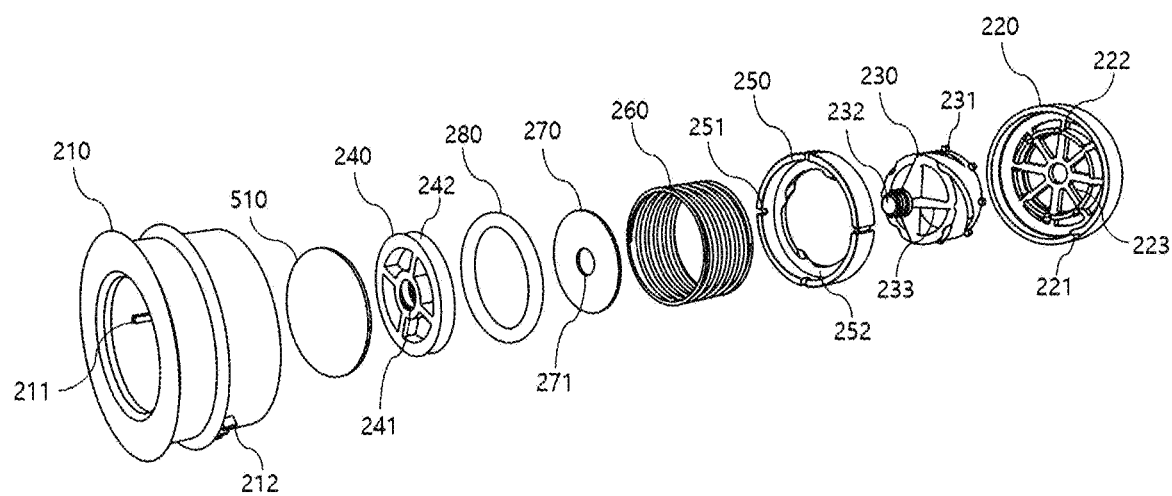
FIG. 4 is a view illustrating a pressure unit of the respiratory muscle strengthening device according to an embodiment of the present invention.

Referring to FIG. 4, the pressure unit 200 includes: a cylindrical frame part 210 having an empty space therein; an adjustment cover 220 provided to surround one end of the frame part 210; a main filler 230 provided inside the frame part 210 to be coupled to the inner circumferential surface of the adjustment cover 220; a sub-filler 240 coupled to the end of the main filler 230; a regulator 250 having a hollow formed therein to be coupled with the main filter 230 by inserting the main filler 230 into the hollow; a spring 260 of which one end is interfered by the regulator 250 and the other end is interfered by the sub-filler 240; a shield 270 rotatably coupled to one side of the end of the main filler 230 and disposed to be parallel to the sub-filler 240; and a sealing member 280 provided between the sub-filler 240 and the frame part 210.

Figure 5:
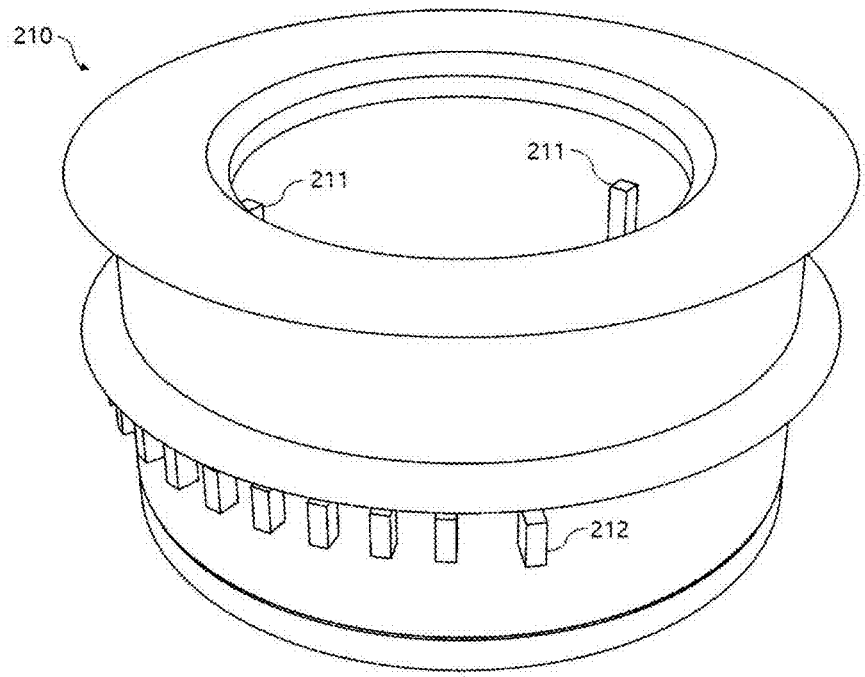
FIG. 5 is a view illustrating a frame unit of the respiratory muscle strengthening device according to an embodiment of the present invention.

Referring to FIG. 5, the frame part 210 has a U-shaped cross-section and has a hollow formed therein, and the sub-filler 240 is inserted into the hollow. In addition, the frame part 210 is inserted and fixed into the fixing part 110 to prevent foreign substances from penetrating into the frame part 210.

The frame part 210 includes a rail part 211 protruding from the inner circumferential surface of the frame part 210 to guide the regulator 250 to be transferred linearly, and a plurality of adjustment protrusions 212 protruding from the outer circumferential surface of the frame part 210. For example, the rail part 211 is coupled to a rail groove 251, which will be described later, and guides the regulator 250 to be linearly moved by the inhalation and exhalation of the user. Additionally, the plurality of adjustment protrusions 212 are radially spaced apart from each other at a predetermined distance along the outer circumferential surface of the frame part 210. In this instance, the plurality of adjustment protrusions 212 interfere with an elastic protrusion 221, which will be described later, to selectively fix the adjustment cover 220.

Figure 6:
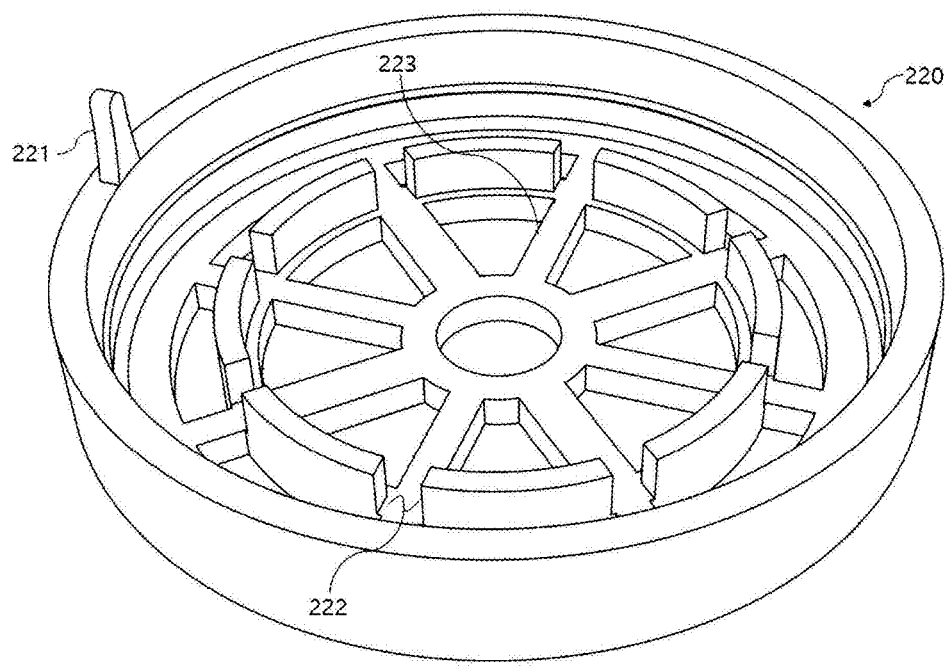
FIG. 6 is a view illustrating an adjustment cover of the respiratory muscle strengthening device according to an embodiment of the present invention.

Referring to FIG. 6, the adjustment cover 220 has a U-shaped cross section and is provided to surround one end of the frame part 210. In this instance, the inner circumferential surface of the adjustment cover 220 is provided with a spiral groove (not shown) or a spiral protrusion (not shown). That is, the adjustment cover 220 is coupled while rotating in a state of being adjacent to a spiral protrusion (not shown) or a spiral groove (not shown) formed on an outer circumferential surface of one side of the frame part 210.

Here, the adjustment cover 220 includes an elastic protrusion 221 protruding from an end of the adjustment cover 220. For example, the elastic protrusion 221 protrudes from the outer circumferential surface of the adjustment cover 220 in a direction facing the adjustment protrusion 212. Therefore, the elastic protrusion 221 is put between the adjustment protrusions 212 neighboring each other to fix the adjustment cover 220. When the adjustment cover 220 is rotated to fix the adjustment cover 220 to the frame part 210, the elastic protrusion 221 is bent above the plurality of adjustment protrusions 212 by elasticity of the elastic protrusion 221. That is, the elastic protrusion 221 is made of a transformable elastic material.

Furthermore, the adjustment cover 220 includes a plurality of insertion grooves 222 radially arranged to fix the main filler 230. In this instance, insertion protrusions 231, which will be described later, are respectively inserted into the plurality of insertion grooves 222, so that the adjustment cover 220 and the main filler 230 are fixed. The plurality of insertion grooves 222 are formed long in the longitudinal direction so that the insertion protrusions 231 do not escape from the insertion grooves 222 even if the main filler 230 is linearly moved.

Moreover, the adjustment cover 220 includes a plurality of cover ribs 223 radially arranged around the center of the adjustment cover 220 so that inhaled air or exhaled air can flow. That is, the plurality of cover ribs 223 are disposed to form an empty space on the outer circumferential surface of the adjustment cover 220 so as to secure rigidity of the adjustment cover 220 and to allow the inhaled air or exhaled air of the user to flow.

Figure 7:
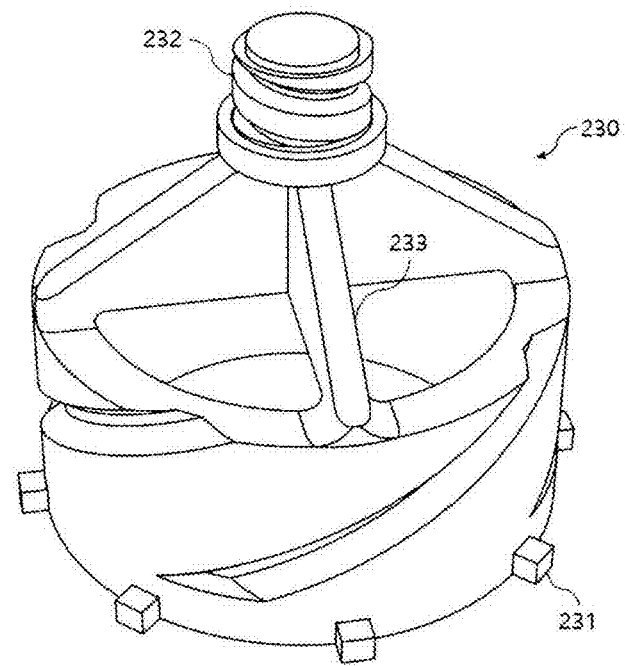
FIG. 7 is a view illustrating a main filler of the respiratory muscle strengthening device according to an embodiment of the present invention.

Referring to FIG. 7, the main filler 230 is inserted into the frame part 210 and is coupled to the adjustment cover 220. In this instance, the main filler 230 includes a plurality of insertion protrusions 231 protruding from the outer circumferential surface of the main filler 230 and arranged radially. The plurality of insertion protrusions 231 are formed in a shape corresponding to that of the plurality of insertion grooves 222, thereby allowing the main filler 230 to be coupled to the adjustment cover 220. Here, the main filler 230 is linearly transferred the spring 260 in the direction of contracting the spring 260 during the user's inhalation, and is linearly transferred in the direction of releasing the spring 260 during the user's exhalation.

Furthermore, the main filler 230 includes a shaft 232 inserted into a through hole 241, which will be described later, and rotatably coupled to a screw thread formed on the inner circumferential surface of the through hole 241. The shaft 232 is formed at the central portion of the main filler 230 to protrude toward the sub-filler 240. In this instance, the shaft 232 has a screw thread formed on the outer circumferential surface of the shaft 232 so as to be rotatably coupled with the through hole 241.

In addition, the main filler 230 includes a plurality of main filler ribs 233 radially arranged around the center of the main filler 230 so that the inhaled air or exhaled air of the user can flow. That is, the plurality of main filler ribs 233 form an empty space in the main filler 230 so as to secure rigidity of the main filler 230 and facilitate flow of the inhaled air or exhaled air of the user.

Additionally, the plurality of main filler ribs 233 are gradually inclined toward the end of the shaft 232 to be gathered toward the center of the shaft 232. Accordingly, when the user inhales air, the shield 270 is bent to be adjacent to the outer circumferential surfaces of the plurality of main filler ribs 233.

Figure 8:
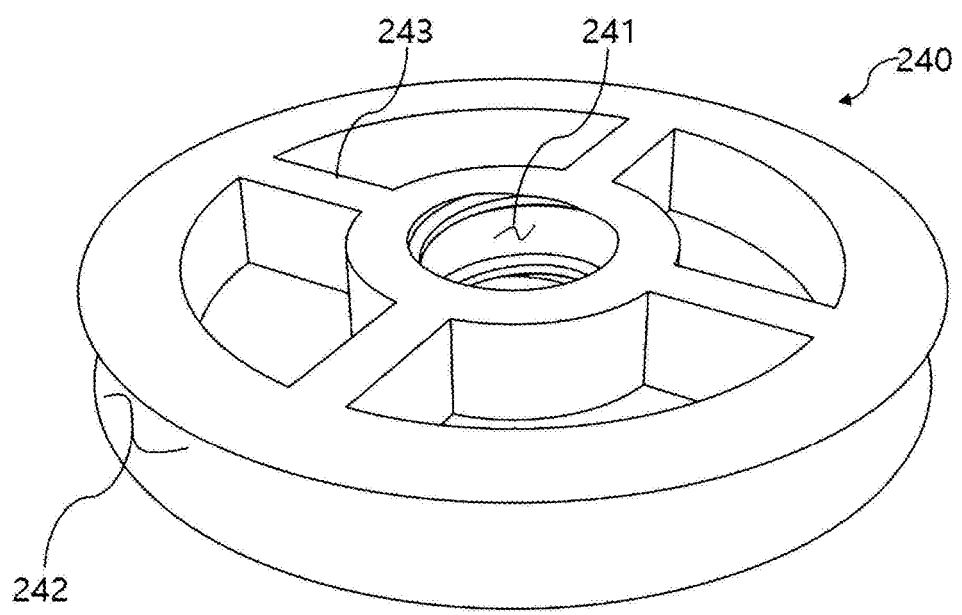
FIG. 8 is a view illustrating a sub-filler of the respiratory muscle strengthening device according to an embodiment of the present invention.

Referring to FIG. 8, the sub-filler 240 is formed in a disc shape and is linearly transferred in the same direction according to the linear transfer of the main filler 230. In addition, the sub-filler 240 includes a through hole 241 penetrating through the central portion of the sub-filler 240, and a sealing groove 242 formed on an outer circumferential surface of the sub-filler 240 to prevent the sealing member 280 from escaping. In this instance, at least a portion of the sub-filler 240 is inserted or withdrawn through the hollow of the frame 210 by the inhalation or exhalation of the user.

In addition, the sub-filler 240 includes a plurality of sub-filler ribs 243 radially arranged around the center of the sub-filler 240 so that the inhaled air or exhaled air of the user can flow. That is, the plurality of sub-filler ribs 243 form an empty space in the sub-filler 240 to secure rigidity of the sub-filler 240 and facilitate the flow of the inhaled air or exhaled air of the user.

Figure 9:
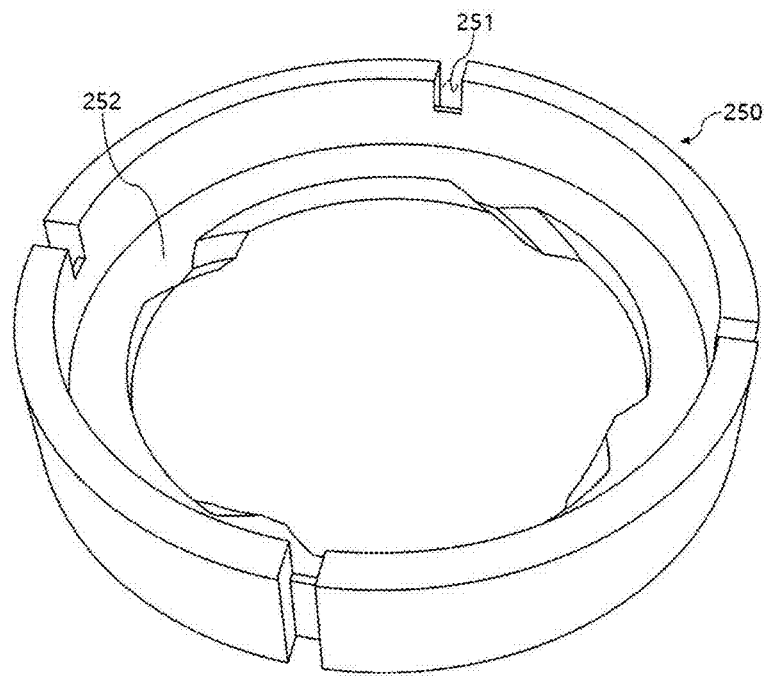
FIG. 9 is a view illustrating a regulator of the respiratory muscle strengthening device according to an embodiment of the present invention.

Referring to FIG. 9, the regulator 250 has a hollow therein, and the hollow of the regulator 250 is formed in a shape corresponding to the outer circumferential surface of the main filler 230. That is, the main filler 230 is inserted into the hollow of the regulator 250. In this instance, the regulator 250 includes a plurality of rail grooves 251 radially arranged around the center of the regulator 250 along the outer circumferential surface of the regulator 250. That is, the rail portion 211 is inserted into at least one of the plurality of rail grooves 251 so that the regulator 250 is linearly moved in the same direction as the main filler 230 according to the linear transfer of the main filler 230.

Moreover, the regulator 250 includes an interference portion 252 formed to protrude from the inner circumferential surface of the regulator 250 toward the center so that the spring 260 can be seated thereon.

Figure 10:
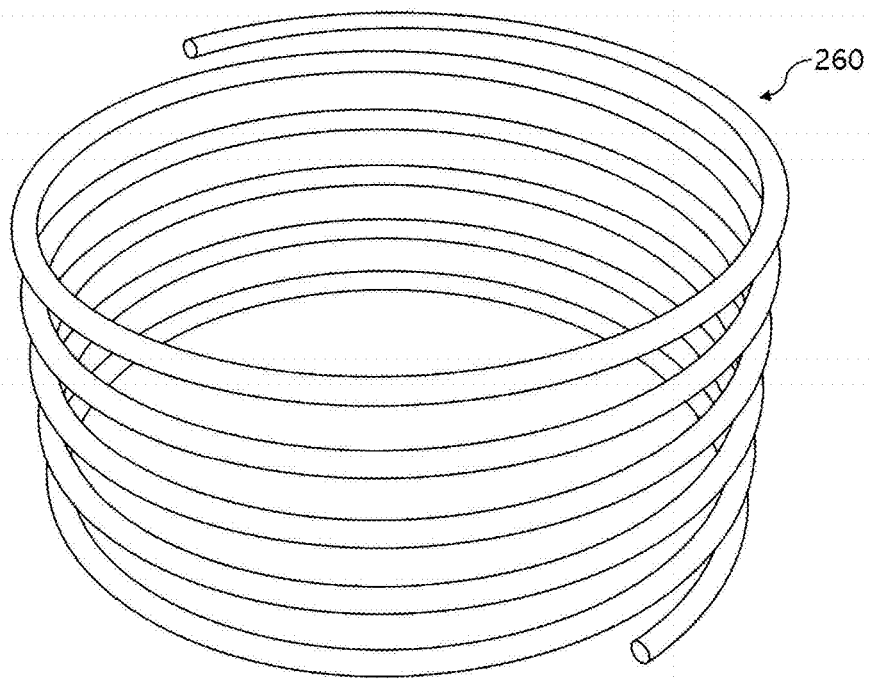
FIG. 10 is a view illustrating a spring of the respiratory muscle strengthening device according to an embodiment of the present invention.

Referring to FIG. 10, the spring 260 is provided between the sub-filler 240 and the regulator 250. That is, one end of the spring 260 is seated on the interference portion 252, and the other end of the spring 260 is seated on the side surface of the sub-filler 240. When the adjustment cover 220 is coupled to the frame part 210, the main filler 230 is compressed while pushing the regulator 250 in one direction.

Figure 11:
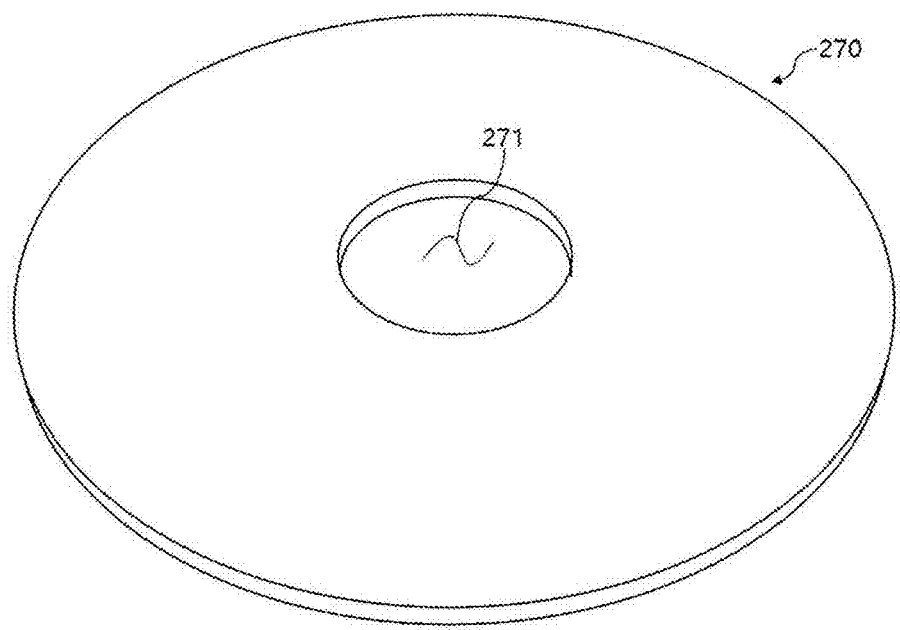
FIG. 11 is a view illustrating a shield of the respiratory muscle strengthening device according to an embodiment of the present invention.

Referring to FIG. 11, the shield 270 is formed in a disc shape between the sub-filler 240 and the regulator 250, and includes an insertion hole 271 provided at the central portion of the shield 270. The shaft 232 is inserted into the insertion hole 271 to fix the shield 270. In addition, the shield 270 is provided in a state of hiding at least a portion of the sub-filler 240. In other words, the shield 270 serves to block the empty space formed between the sub-filler ribs 243. At this time, the shield 270 is formed of an elastic material in a thin plate shape. Accordingly, the shield 270 is bent during the exhalation of the user, and is returned to its original state when the exhalation is finished. That is, the shield 270 induces the user to inhale air with pressure stronger than elasticity of the shield 270, thereby enabling the user to do an exhalation motion during the respiratory motion. Here, the shield 270 is bent in a direction adjacent to the outer circumferential surface of the main filler 233 when the user inhales air. For example, the shield 270 is formed of a silicon material.

Figure 12:
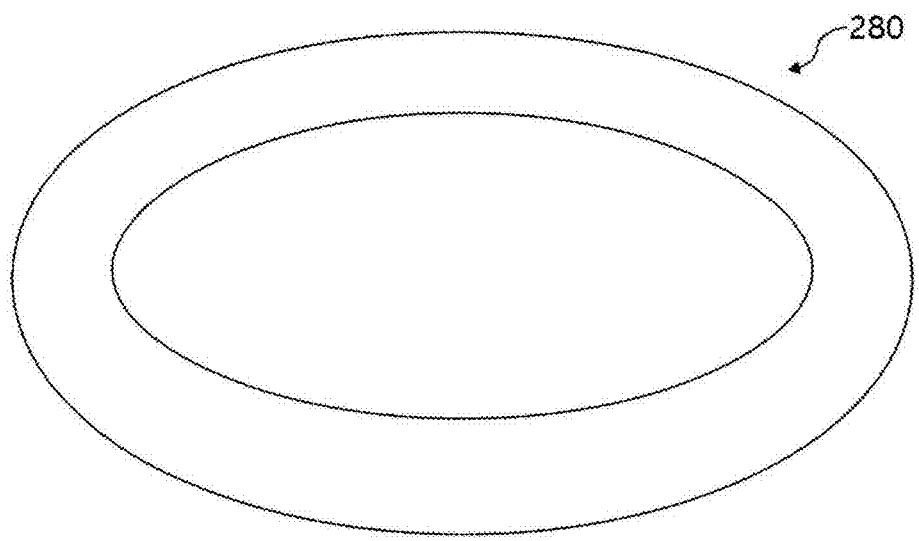
FIG. 12 is a view illustrating a sealing member of the breathing muscle strengthening apparatus according to an embodiment of the present invention.

Referring to FIG. 12, the sealing member 280 is made of a rubber material to block a gap between the sub-filler 240 and the frame part 210. At this time, the sealing member 280 is provided along the outer circumferential surface of the sub-filler 240. That is, the sealing member 280 is provided in a state in which the sealing member 280 is seated on the sealing groove 242.

Figure 13:
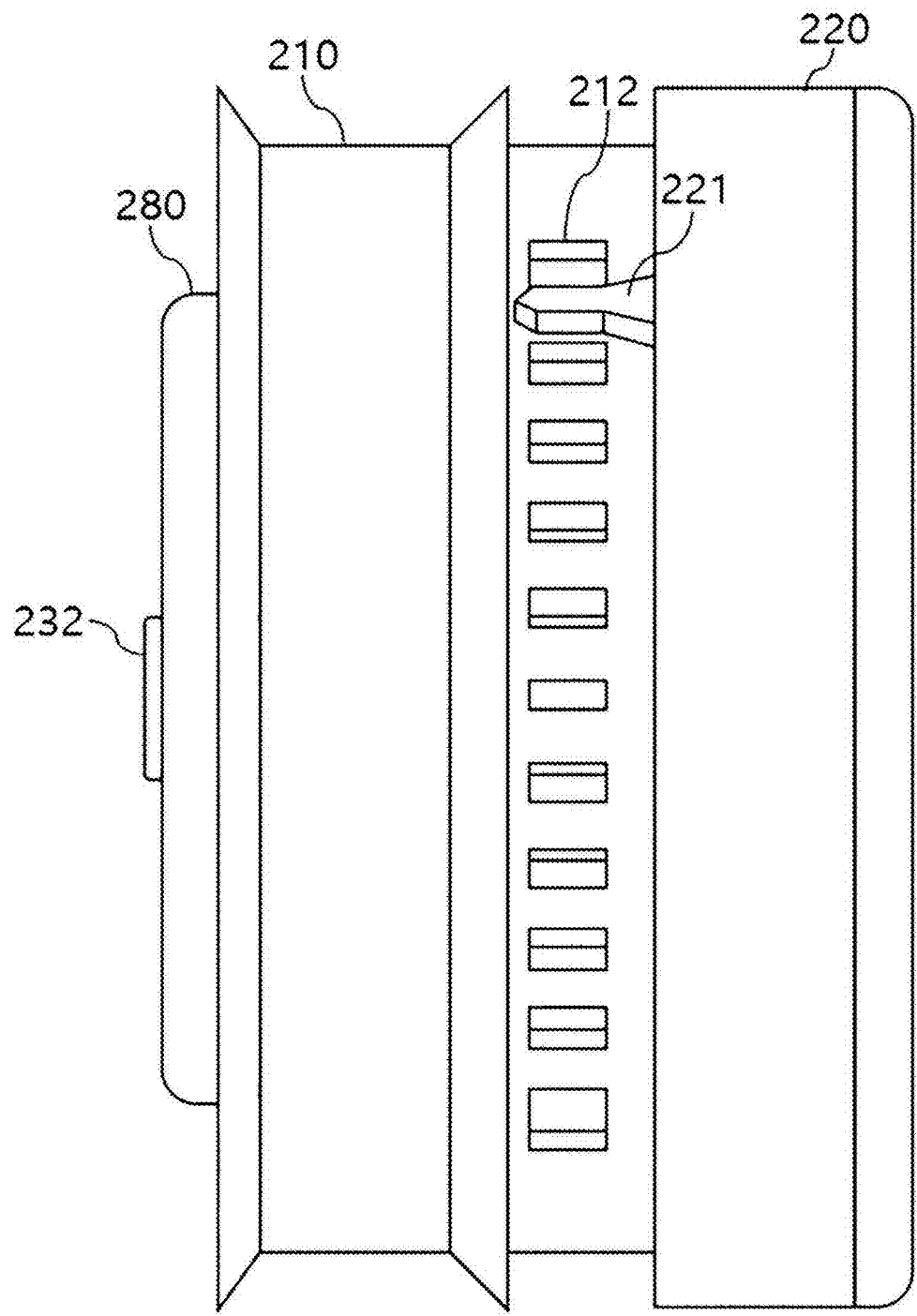
FIG. 13 is a side view illustrating a pressure unit of the respiratory muscle strengthening device according to an embodiment of the present invention.

Referring to FIG. 13, the adjustment cover 220 adjusts a compression state of the spring 260 according to a distance between the adjustment cover 220 and the frame part 210. That is, when the adjustment cover 220 is coupled to the frame part 210, the distance between the adjustment cover 220 and the frame part 210 is adjusted according to the number of rotations of the adjustment cover 220, thereby adjusting the degree of compression of the spring 260. For example, when the adjustment cover 220 is rotated in one direction in the state in which the adjustment cover 220 and the frame part 210 are coupled, the adjustment cover 220 pushes the main filler 230 in the direction of the frame part 210 so that the main filler 230 is linearly moved. When the main filler 230 is linearly moved toward the frame part 210, the regulator 250 is also transferred in the same direction. Accordingly, the spring 260 is compressed. That is, since inhalation of the user can be more easily performed, the amount of respiratory motion is decreased. In contrast, when the adjustment cover 220 is rotated in the opposite direction in the state in which the adjustment cover 220 and the frame part 210 are coupled to each other, the adjustment cover 220 pulls the main filler 230 in the opposite direction of the frame part 210 so that the main filler 230 is linearly moved. When the main filler 230 is linearly moved in the opposite direction to the direction facing the frame part 210, the regulator 250 is also transferred in the same direction. Accordingly, the spring 260 is tensioned. In other words, since it is difficult for the user to inhale air, the amount of respiratory motion is increased. As a result, the respiratory muscle strengthening device according to the present invention can adjust the respiration strength of the user by changing the state of the spring 260 through rotation of the adjustment cover 220.

Figure 14:
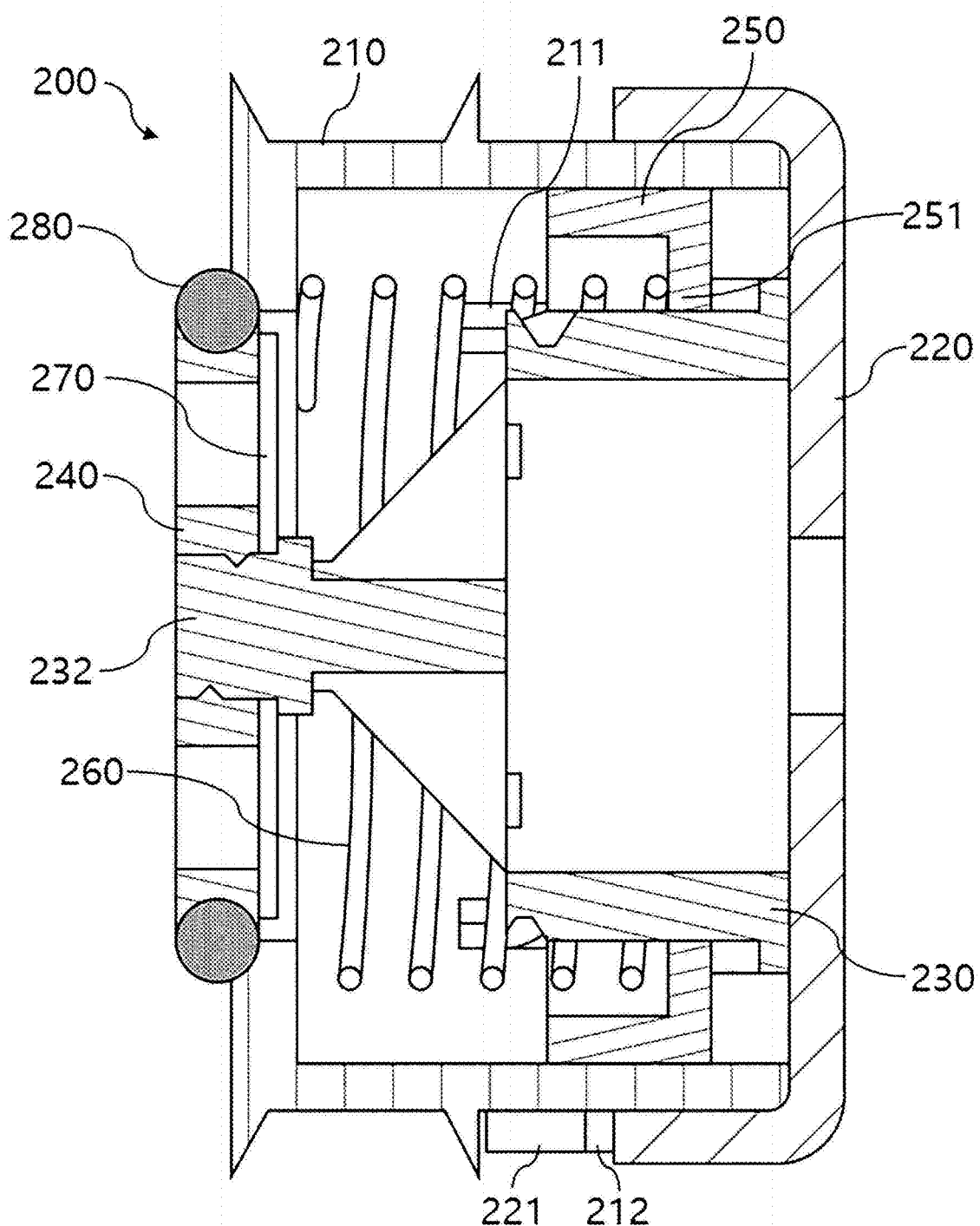
FIG. 14 is a cross-sectional view illustrating the pressure unit of the respiratory muscle strengthening device according to an embodiment of the present invention.
Figure 15:
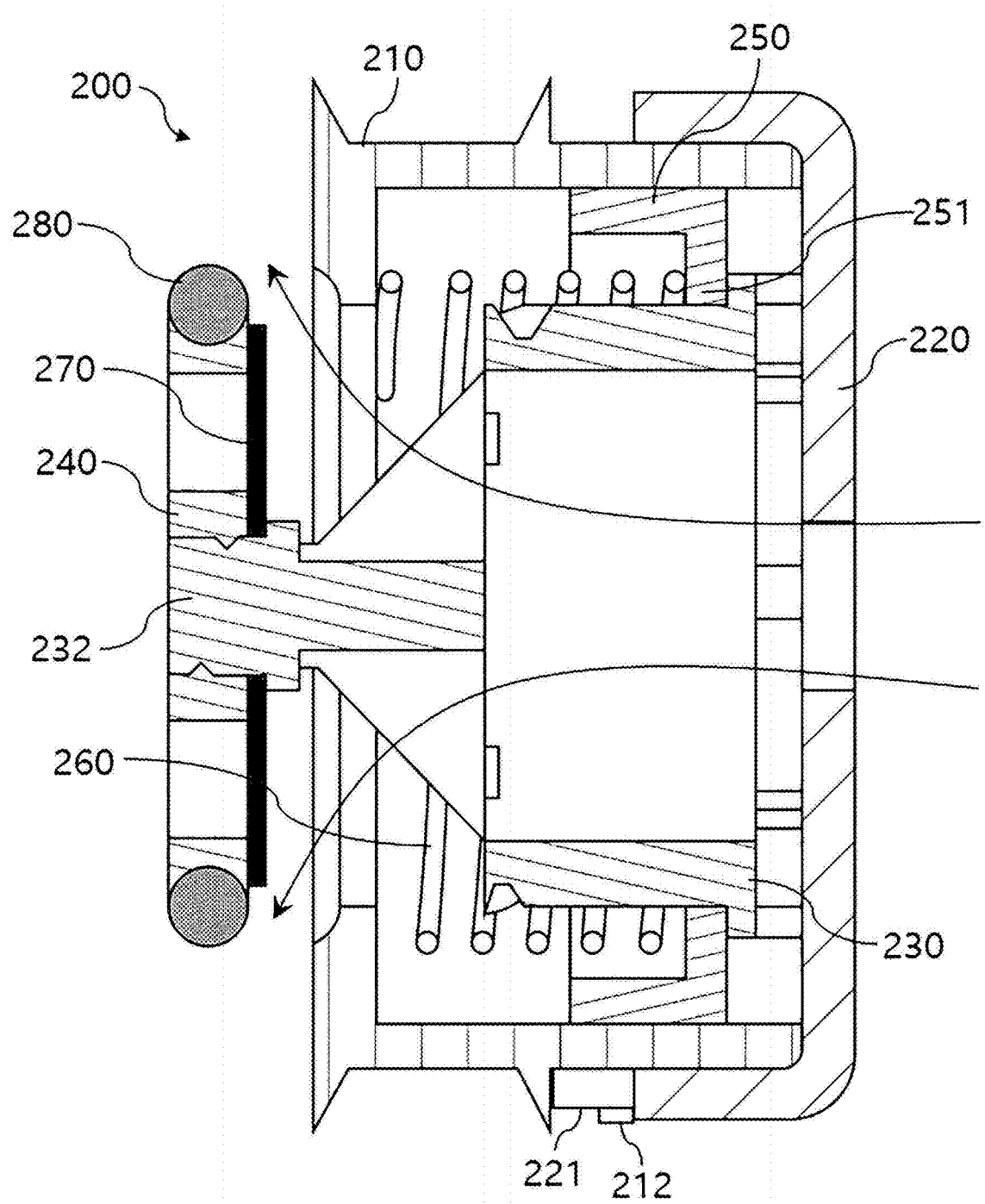
FIG. 15 is a cross-sectional view illustrating an operation of the pressure unit at the time of inhalation of the respiratory muscle strengthening device according to an embodiment of the present invention.
Figure 16:
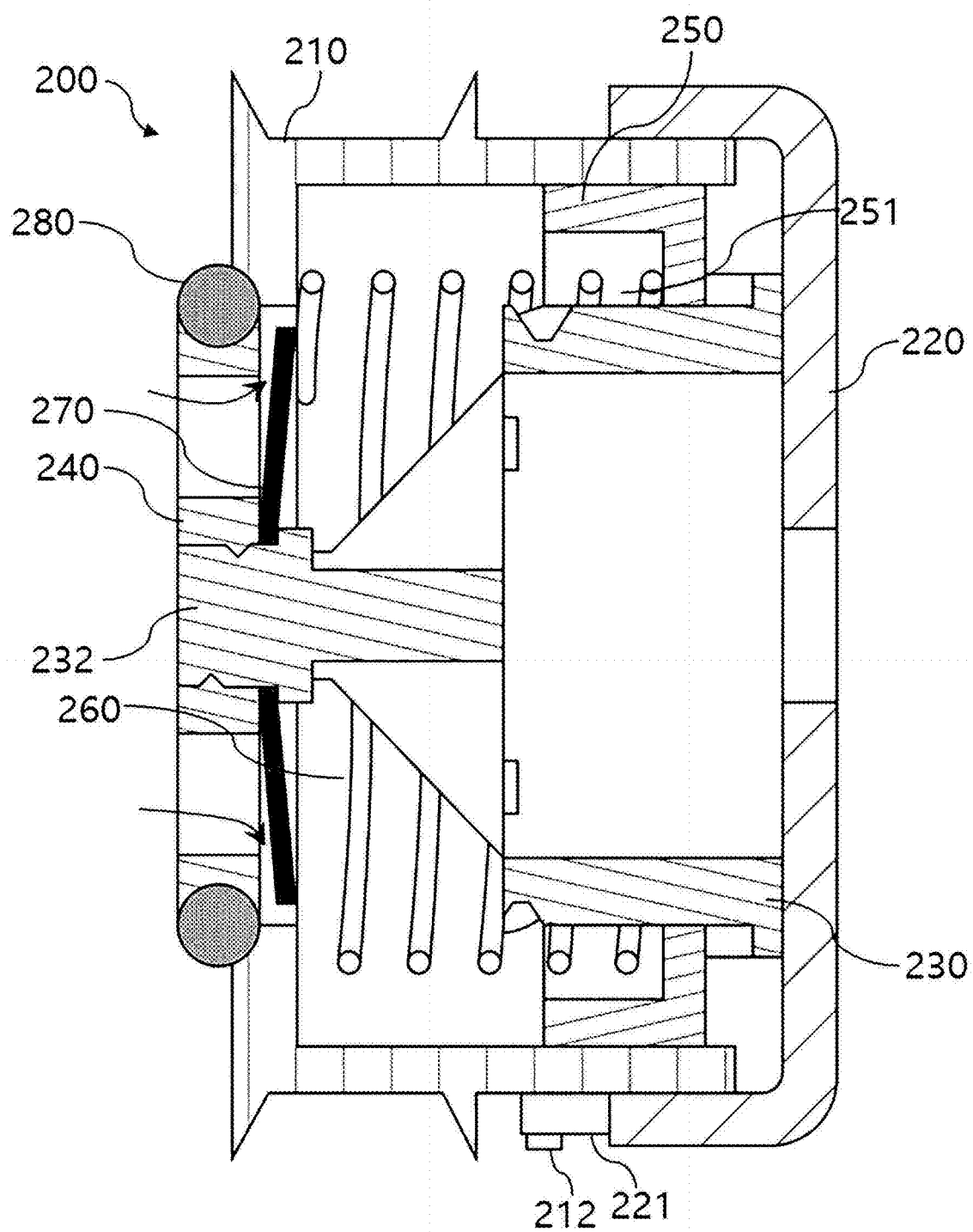
FIG. 16 is a cross-sectional view illustrating an operation of the pressure unit at the time of exhalation of the respiratory muscle strengthening device according to an embodiment of the present invention.

Referring to FIGS. 14 to 16, since outside air can pass through the pressure unit 200 only when the user inhales air with pressure stronger than the elasticity of the spring 260, the user can perform an inhalation motion during the respiratory motion.

More specifically, when the user wears the respiratory muscle strengthening device according to the present invention in a state in which the pressure unit 200 is coupled to the fixing portion 110, the flow of air is controlled by the pressure unit 200, a flow of air is controlled by the pressure unit 200. First, during the user's inhalation, outside air is introduced and is stopped by the shield 270. In this instance, when the user performs the inhalation motion at pressure exceeding the elasticity of the spring 260, the sub-filler 240 is drawn out of the hollow of the frame part 210, and a flow path is formed between the sub-filler 240 and the frame part 210. That is, only when the user performs the inhalation motion at pressure exceeding the elasticity of the spring 260, at least a portion of the sub-filler 240 is drawn out of the hollow of the frame part 210 to form a flow path, thereby allowing outside air to flow therein. After that, when the user stops inhalation, the sub-filler 240 is inserted into the hollow of the frame part 210 by the elasticity of the spring 260 to return to the original state.

Furthermore, in the case of the user's exhalation, the internal air flows, and then, is stopped by the shield 270. In this instance, when the user performs the exhalation motion at pressure exceeding the elasticity of the shield 270, the shield 270 is bent to form a flow path between the shield 270 and the sub-filler 240. That is, only when the user performs the exhalation motion at pressure exceeding the elasticity of the shield 270, the shield 270 is bent toward the main filler 230 and at least a portion of the sub-filler 240 is opened to form a flow path, so that the inside air can flow to the outside.

TABLE 1

| Male | in tens | in twenties | in thirties | in forties | in fifties | in sixties |
|---|---|---|---|---|---|---|
| MIP (cmH$_2$O) | 115.9 | 111.8 | 107.7 | 103.6 | 99.5 | 95.4 |
| 30% MIP | 34.77 | 33.54 | 32.31 | 31.08 | 29.85 | 28.62 |

TABLE 2

| Female | in tens | in twenties | in thirties | in forties | in fifties | in sixties |
|---|---|---|---|---|---|---|
| MIP (cmH$_2$O) | 101.9 | 95.8 | 89.7 | 83.6 | 77.5 | 71.4 |
| 30% MIP | 30.57 | 28.74 | 26.91 | 25.08 | 23.25 | 21.42 |

TABLE 3

|  | Runner | Swimmer |
|---|---|---|
| MIP (cmH$_2$O) | 134 | 115 |
| 80% MIP | 107.2 | 92 |

In addition, Tables 1 and 2 show average respiratory pressure values for each age group, and exercise values suitable for the average respiratory pressure values. 30% of the pressure value is appropriate for an ordinary person, and 80% of the pressure value is appropriate for an athlete. The pressure value can be adjusted in the range from 20 to 100 cmH$_2$O through the spring 260.

As a result, the user can perform the respiratory motion by using the spring 260 and the shield 270, and can adjust the strength of the respiratory motion by replacing the spring 260 and the shield 270. In addition, the respiratory muscle strengthening device according to the present invention can allow the user to focus on any one among the inhalation motion and the exhalation motion by coupling any one among the spring 260 and the shield 270. For instance, in a case in which the spring 260 is coupled to the pressure unit 200 but the shield 270 is not coupled, the user can focus on the inhalation motion. On the contrary, in a case in which the spring 260 is not coupled to the pressure unit 200 but the shield 270 is coupled, the user can focus on the exhalation motion.

Figure 17:
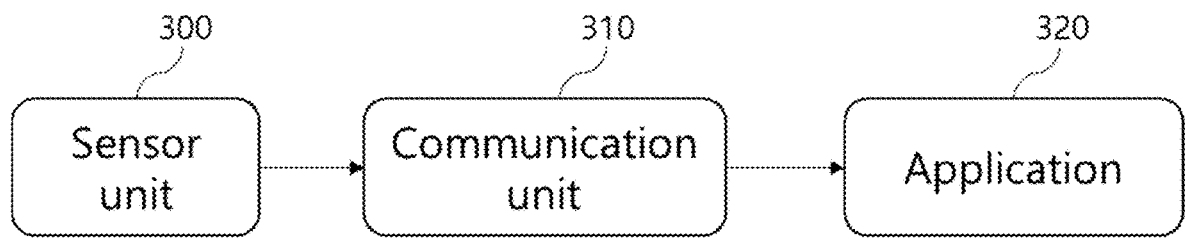
FIG. 17 is a view illustrating a control flow of a sensor unit of the respiratory muscle strengthening device according to an embodiment of the present invention.

Next, the sensor unit 300 is provided. Referring to FIG. 17, the sensor unit 300 is detachably mounted on the fixing part 110 and measures and transmits the respiration pattern of the user. In addition, the sensor unit 300 serves to measure pressure and a flow rate of the inhaled air or the exhaled air of the user, and can be provided in any form if the user can measure the pressure and flow rate of the user. For example, the sensor unit 300 is a pressure sensor for measuring lung capacity of the user.

In this instance, the sensor unit 300 includes a communication unit 310 for transmitting a measurement value of the sensor unit 300 to a terminal, and an application 320 for analyzing the respiration pattern of the user based on the measurement value transmitted from the communication unit 310. The communication unit 310 performs wireless communication using Bluetooth, Wi-Fi, NFC, or the like.

The application 320 analyzes the user's respiration based on the measurement value and provides an appropriate exercise schedule to the user. Furthermore, the application 320 displays the analysis result and the exercise schedule.

The sensor unit 300 includes a light-emitting unit (not shown) indicating a charging state, an operation state, and the like of the sensor unit 300, and a supply unit (not shown) for supplying power to the sensor unit 300.

More specifically, the light-emitting unit is formed of an LED lamp or the like and emits light with different colors according to the charging state and the operation state of the sensor unit 300 so that the user can easily check the state of the sensor unit 300 with eyes. For instance, the light-emitting unit does not emit light at ordinary times but emits light with a predetermined color when the user measures inhalation or exhalation, so that the user can check whether or not the user's inhalation or exhalation is measured well.

Additionally, the communication unit 310 is disposed to transmit and receive wireless signals with one or more external devices, and includes at least one among a Bluetooth chip, a Wi-Fi chip, an NFC chip, and a wireless communication chip (LTE chip). According to an embodiment of the present invention, the communication unit 310 performs communication with an external terminal by using a Bluetooth chip, which is a short range communication method, but performs communication with the terminal using a long distance communication method.

In addition, the supply unit includes one or more chargeable batteries embedded to provide a power source or a power module which can receive external power on a wire.

Furthermore, the application 320 is provided. The application 320 analyzes the user's respiration based on the measurement value of the sensor unit 300 and provides an exercise schedule suitable for the user.

Additionally, the application 320 outputs exercise schedule management, exercise state feedback, exercise result analysis, calorie consumption by the respiratory motion, etc. to the user's terminal, such as a smartphone, on the basis of information on the user's respiration transmitted from the communication unit 310. In this instance, the application 320 serves to output the analysis result and the exercise schedule or the like. That is, the application 320 can indicate the user's lung capacity into a digital numerical value through the value calculated by the sensor unit 300, and can output exercise schedule management, exercise state feedback, and exercise result analysis to the user's terminal, such as a smartphone.

In addition, the application 320 can receive and confirm the exercise schedule management, exercise state feedback, exercise result analysis, etc. in real time. As an example, the user can perform the respiratory motion, measure the maximum inhalation pressure and the maximum exhalation pressure, and inquire the user's use record after executing the application 320.

Figure 18:
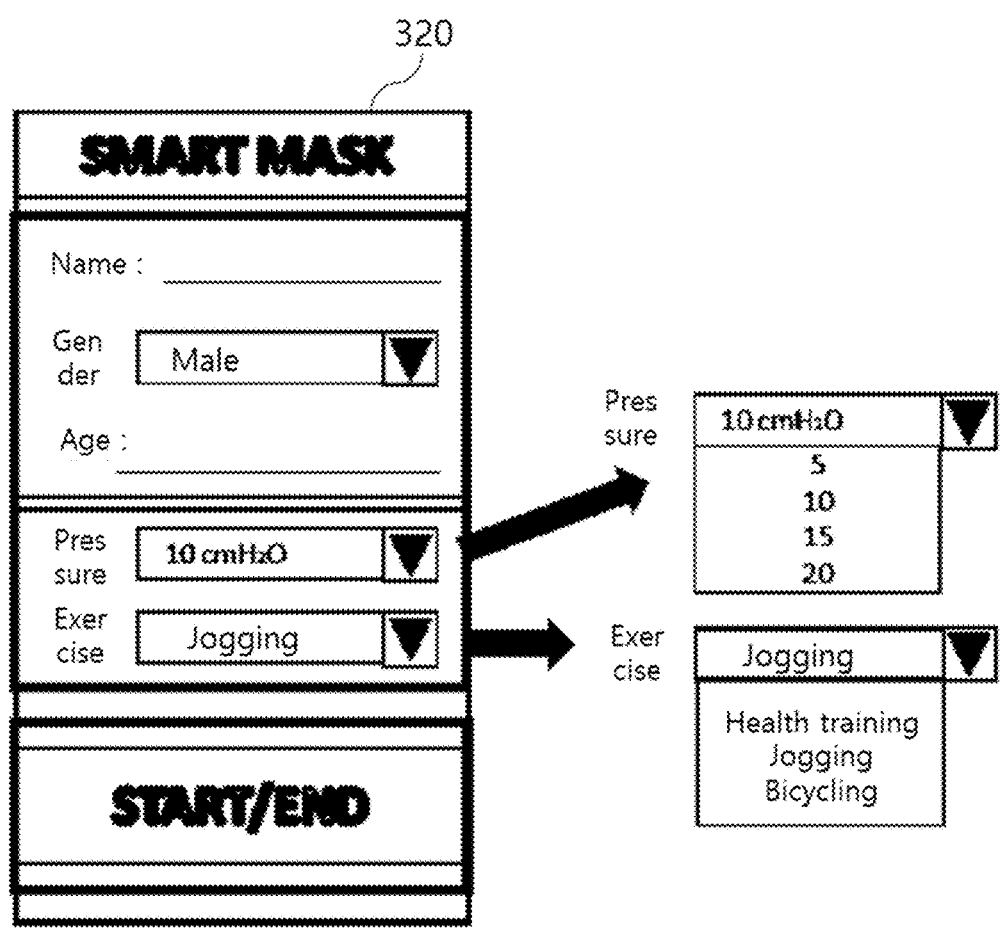
FIG. 18 is a view illustrating a configuration of an application of the respiratory muscle strengthening device according to an embodiment of the present invention.
Figure 19:
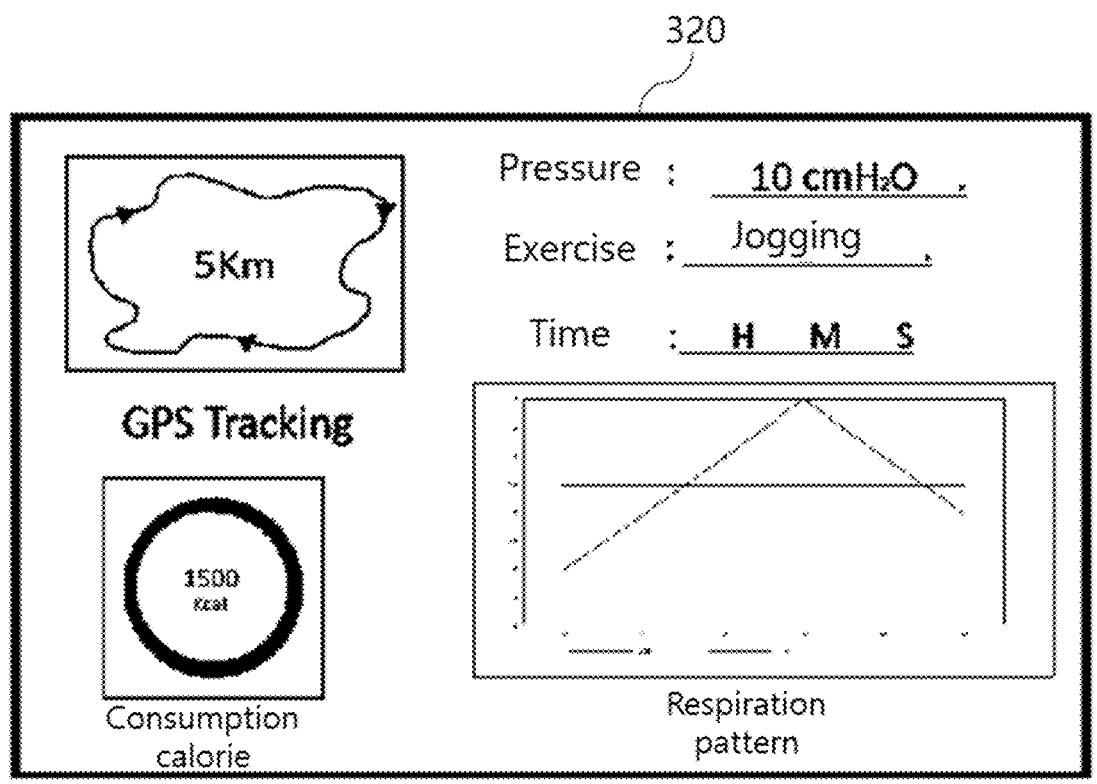
FIG. 19 a view illustrating a configuration of an application of the respiratory muscle strengthening device according to an embodiment of the present invention.
Figure 20:
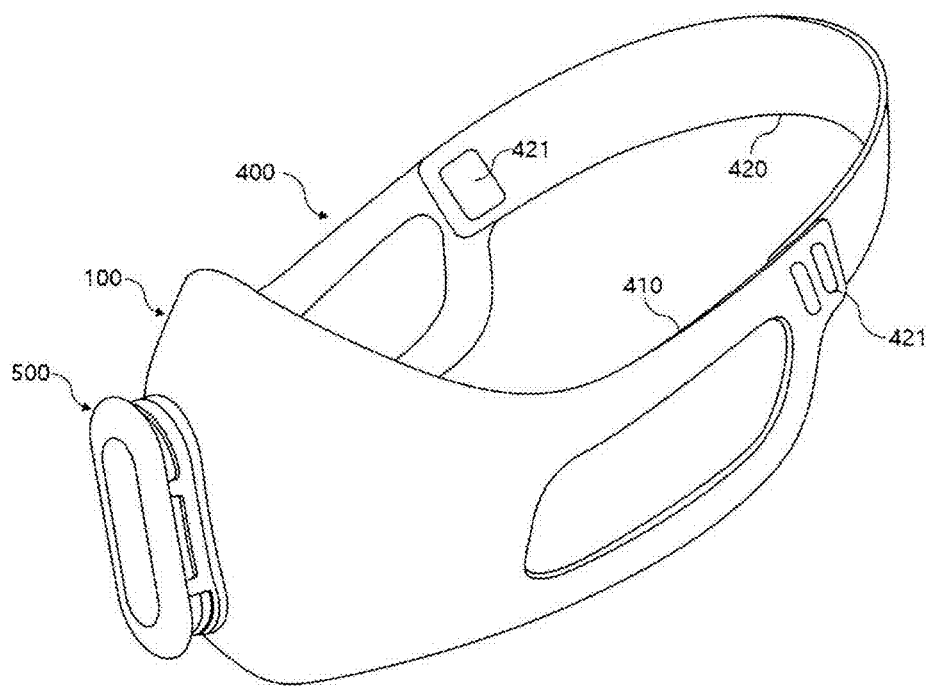
FIG. 20 is a view illustrating a band unit of the respiratory muscle strengthening device according to an embodiment of the present invention.
Figure 21:
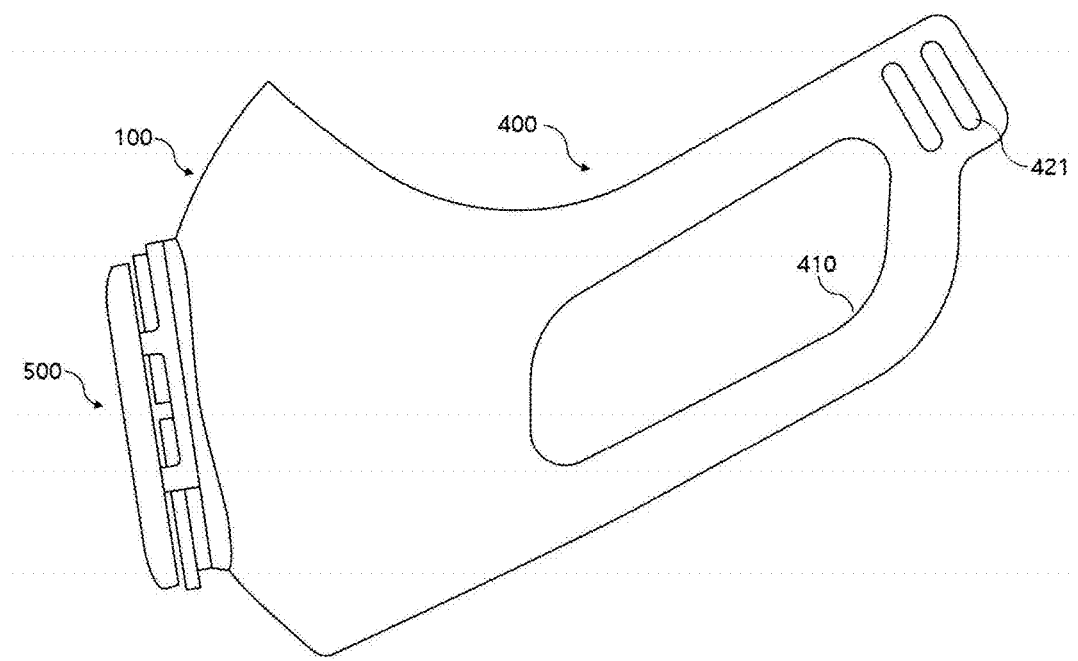
FIG. 21 is a view illustrating the band unit of the respiratory muscle strengthening device at ordinary times.
Figure 22:
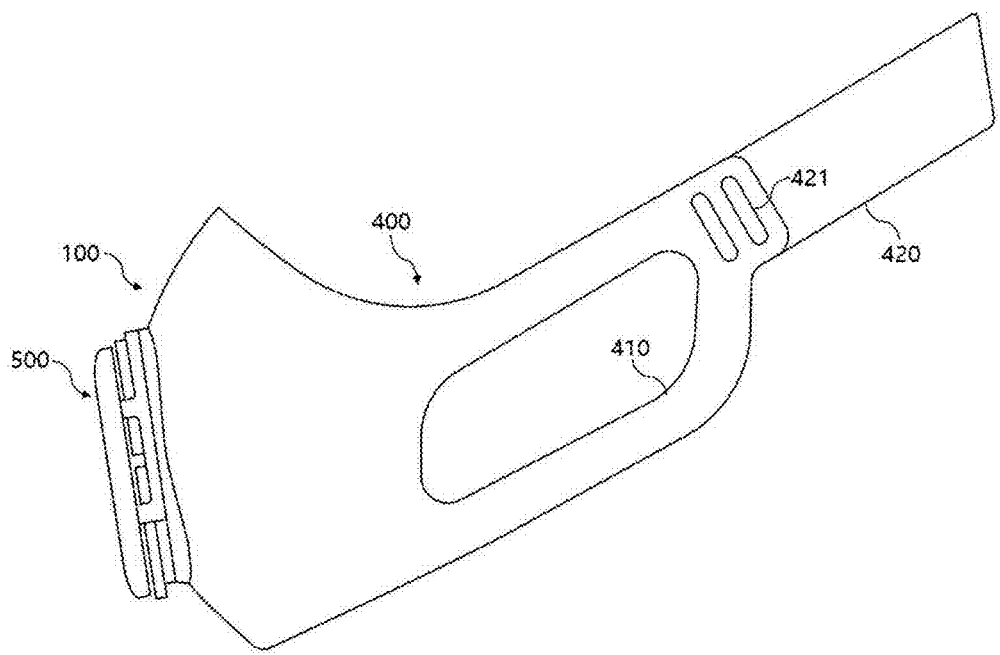
FIG. 22 is a view illustrating the band unit of the respiratory muscle strengthening device during exercise according to an embodiment of the present invention.
Figure 23:
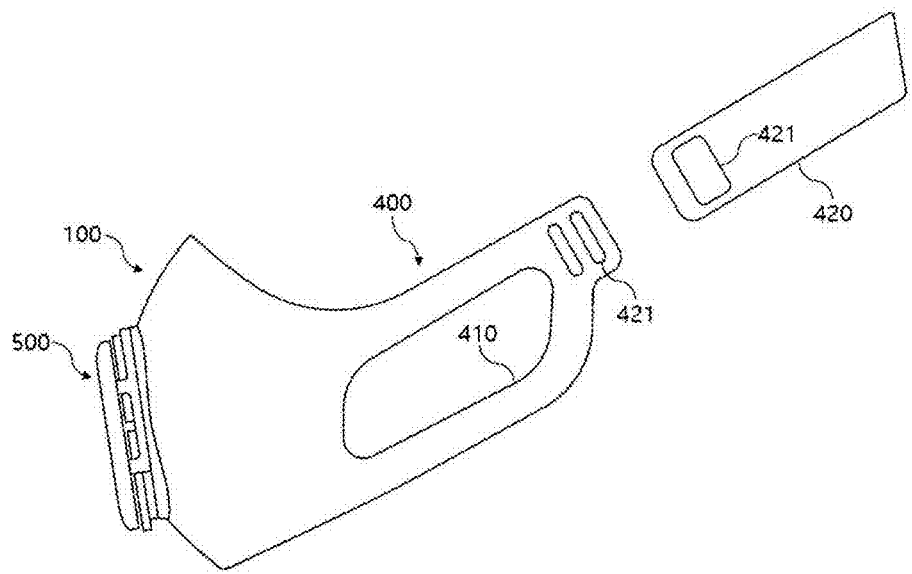
FIG. 23 is a view illustrating the band unit of the respiratory muscle strengthening device according to an embodiment of the present invention, wherein an ear loop part and an extension part are separated from each other.

Referring to FIGS. 18 and 19, the user registers the user information, the pressure value, and the exercise type through a screen of the application 320. In this instance, the user information can be stored by being classified into a plurality of pieces, and the exercise type is, for example, health training, jogging, bicycling, or the like. After the user information is registered, the user executes taps for GPS, consumption calorie, respiration pattern, etc. to perform the respiratory motion and respiration measurement. Here, the sensor unit 300 includes a global positioning system (GPS) sensor for measuring the location of the sensor unit 300.

For example, in a case in which the user executes a respiration pattern tab, the user can check information such as the highest record and the average record, and for example, recent respiratory motions of three times and measurement values can be output. In addition, through a graph having a horizontal axis of time and a vertical axis of pressure, an average value can be calculated so that the user can see the recent respiratory motions and measurement values at a glance. Furthermore, the calculated graph is automatically stored into a file to be transmitted/received. Finally, the present invention proposes a method of analyzing the calculated graph, outputting the user's strengths and weaknesses and reproducing the shape of the graph showing the optimal respiration.

In addition, in a case in which the user executes the consumed calorie tap, the user can see the respiratory motions and measurement values for each time stored till now. For example, when the user clicks exercise time of 30 seconds, the user can check information such as the maximum inhalation pressure, the average inhalation pressure, the maximum exhalation pressure, the average exhalation pressure, and the total exercise time. In this instance, records of the respiratory motion and measurement are automatically stored when the user do exercise for three seconds or more.

Moreover, in a case in which the user executes the GPS tap, the user can check the user's movement distance and movement route, and can grasp the user's position according to exercise time of the user.

As a result, the user can continuously progress the respiratory motion and measurement through the application 320 without feeling tedium, and children can perform the respiratory motion and measurement with interest.

Next, the band unit 400 is provided. The band unit 400 extends from both ends of the mask body 100. In this instance, the band unit 400 makes the mask body 100 get in contact with the face of the user, so that the mask body 100 can be fixed to the face of the user.

For example, referring to FIGS. 20 to 23, the band unit 400 is formed of a strap buckle type. More specifically, the band unit 400 includes ear loop portions 410 respectively extending from both end portions of the mask body 100 to be fixed to the ears of the user, and an extension portion 420 detachably attached to end portions of the ear loop portions 410. In this instance, the ear loop portions 410 and the extension portion 420 can be attached and detached through buckles 421. So, the mask body 100 is usually fixed to the face of the user using only the ear loop portions 410, but, at the time of exercise, the extension portion 420 is attached to the ear loop portions to surround the back of the head of the user so that the mask body 100 can be in close contact with the face of the user.

Figure 24:
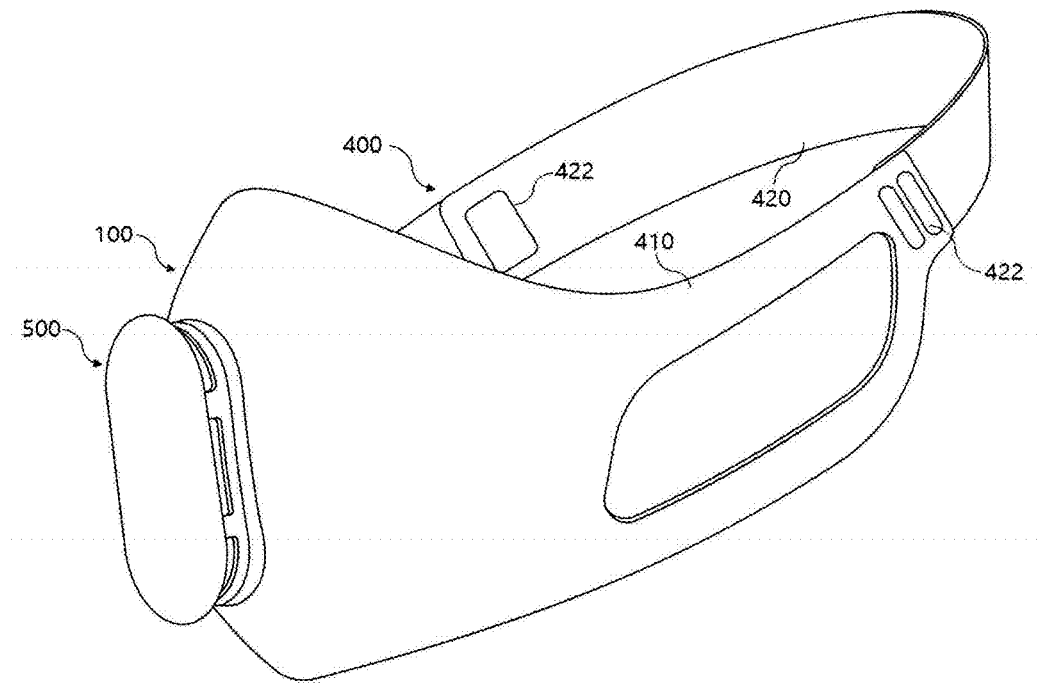
FIG. 24 is a view illustrating a band unit of a respiratory muscle strengthening device during exercise according to another embodiment of the present invention.

Referring to FIG. 24, the extension portion 420 can be more easily detached from and attached to the ear loop portions 410 through a Velcro 422.

Figure 25:
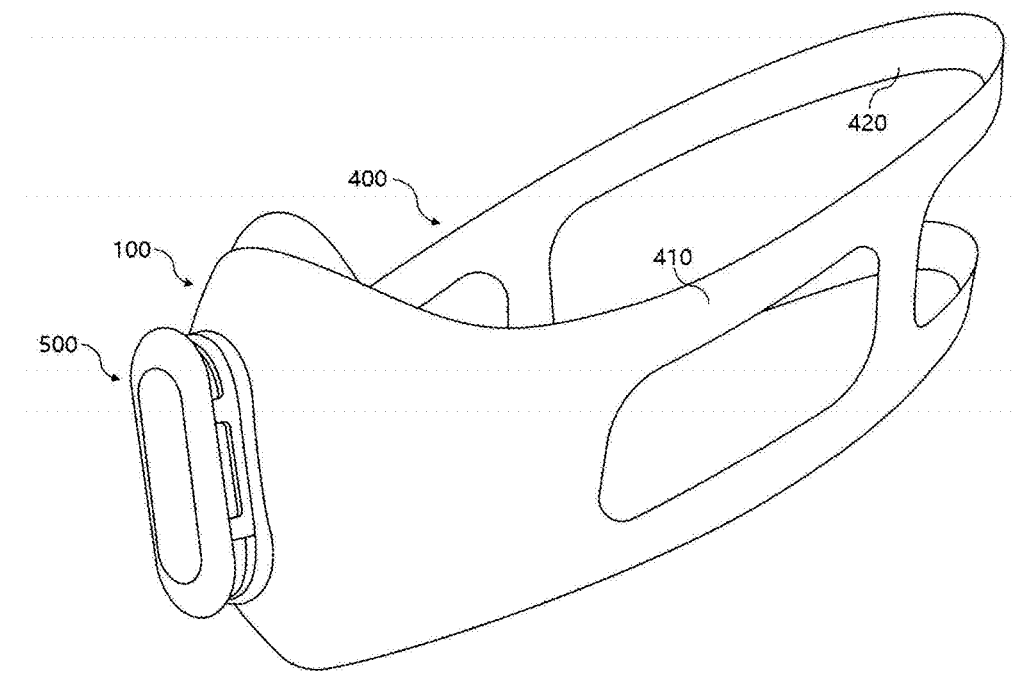
FIG. 25 is a view illustrating a band unit of a respiratory muscle strengthening device during exercise according to another embodiment of the present invention.

Additionally, referring to FIG. 25, the ear loop portions 410 and the extension portion 420 are formed integrally to reduce time required for attachment and detachment and costs required for manufacturing.

Next, the cover unit 500 is provided. The cover unit 500 is detachably attached to the fixing portion 110 in a manner to surround the outer circumferential surface of the fixing portion 110, and is formed in any shape if the cover unit 500 can be attached to or detached from the fixing portion 110.

Here, the cover unit 500 includes a filtering portion 510 for filtering particles in the air. The filtering portion 510 is, for example, a HEPA filter, and as occasion demands, the filtering portion 510 is selectively attached to and detached from the cover unit 500 to protect the respiratory organs of the user. That is, in a case in which the concentration of fine dust is high, when the user performs the respiratory motion after attaching the filtering portion 510 to the cover unit 500, the cover unit 500 can protect the respiratory organs of the user.

Figure 26:
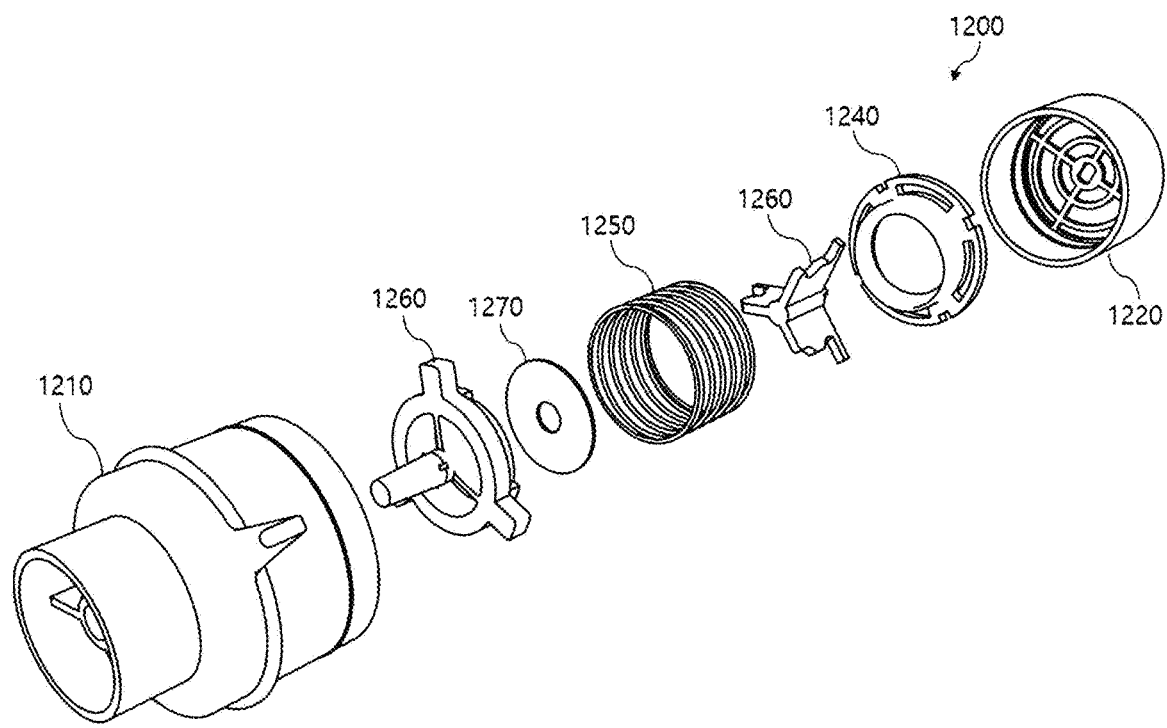
FIG. 26 is a view illustrating a pressure unit of a respiratory muscle strengthening device during exercise according to another embodiment of the present invention.
Figure 27:
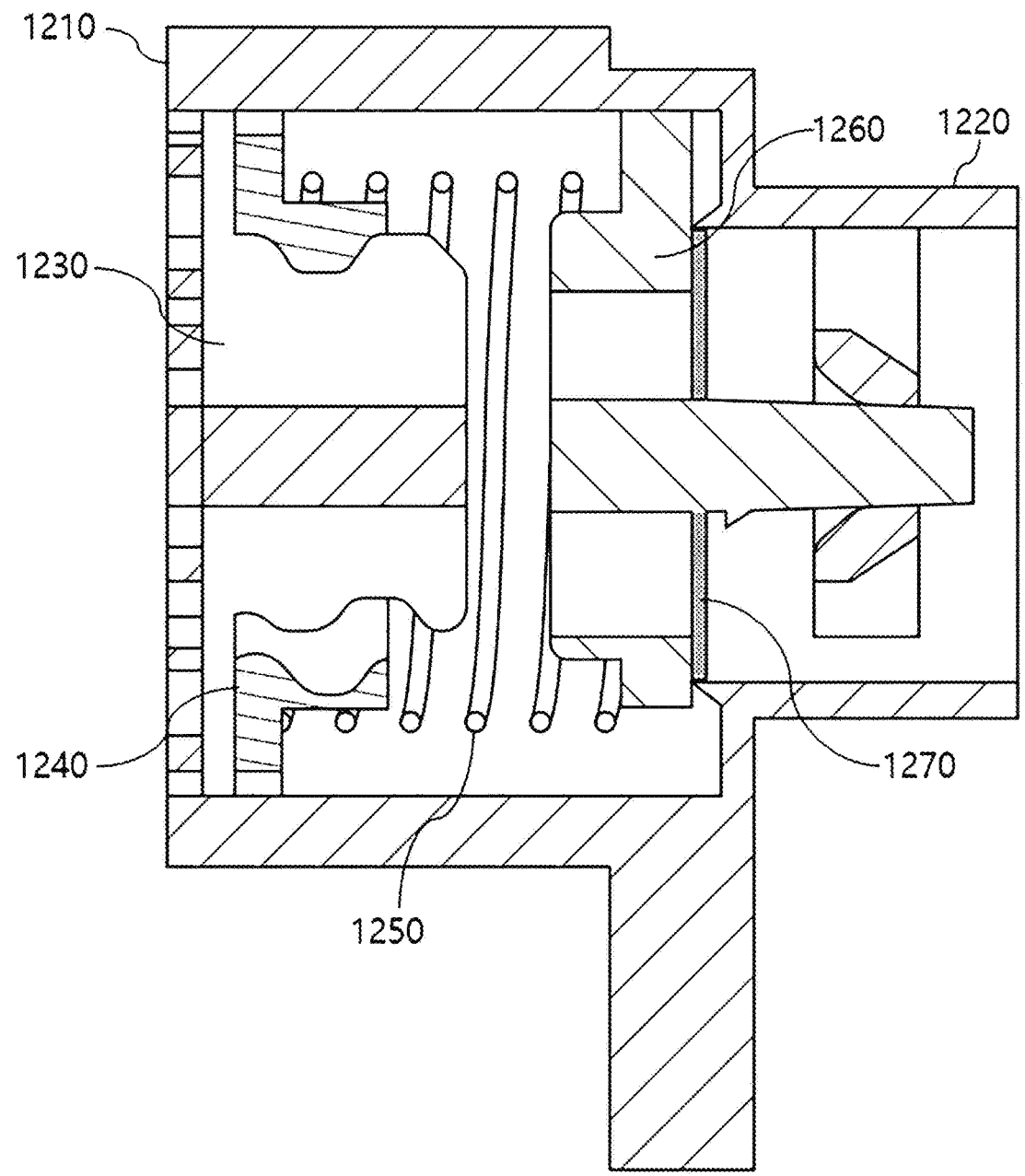
FIG. 27 is a cross-sectional view illustrating the pressure unit of the respiratory muscle strengthening device according to the another embodiment of the present invention.

Referring to FIGS. 26 and 27, a pressure unit 1200 includes a body 1210, a cover 1220, a filler 1230, a regulator 1240, a spring 1250, a disk frame 1260, and a silicon 1270.

First, the body 1210 is provided to fix the pressure unit 1200 to the mask body 100. The cover 1220 is provided to the position of the regulator 1240 when the user rotates the cover 1220. In addition, the filler 1230 serves as a rotation shaft of the regulator 1240. The regulator 1240 is rotated around the filler 1230 according to the rotation of the cover 1220 to adjust the elasticity of the spring 1250. In addition, the spring 1250 serves to generate pressure by elasticity between the regulator 1240 and the disk frame 1260. Furthermore, the disc frame 1260 is coupled with the silicon to maintain a sealed state. When the user performs inhalation at pressure exceeding the pressure of the spring 1250, the disc frame 1260 is transferred in one direction to open a flow path. In addition, the silicon 1270 is adhered to the disk frame 1260 to maintain sealing when the user performs inhalation, and discharges exhaled air without any resistance when the user performs exhalation. That is, the pressure unit 1200 can minimize the cost required for manufacturing the pressure unit by having the optimized configuration for exhalation training, and can allow the user to intensively perform exhalation training.

Next, the pressure unit 200 is coupled to the mouthpiece unit 600 to allow the respiratory motion. In addition, the pressure unit 200 is provided between the mouthpiece unit 600 and the chest wall vibration unit 700 to perform an inhalation muscle strengthening motion through pressure at the time of inhalation and to discharge sputum through the chest wall vibration at the time of exhalation.

Figure 28:
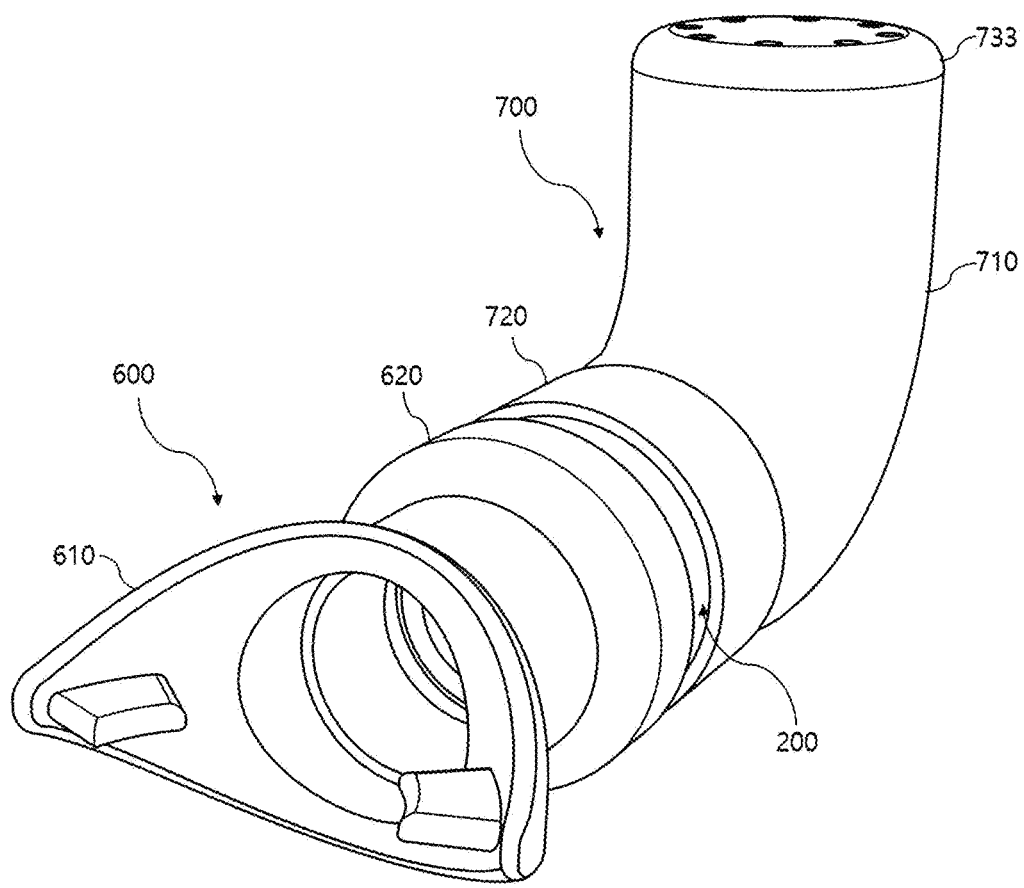
FIG. 28 is a perspective view illustrating a state in which the pressure unit is disposed between a mouthpiece unit and a chest wall vibration unit of the respiratory muscle strengthening device according to the another embodiment of the present invention.
Figure 29:
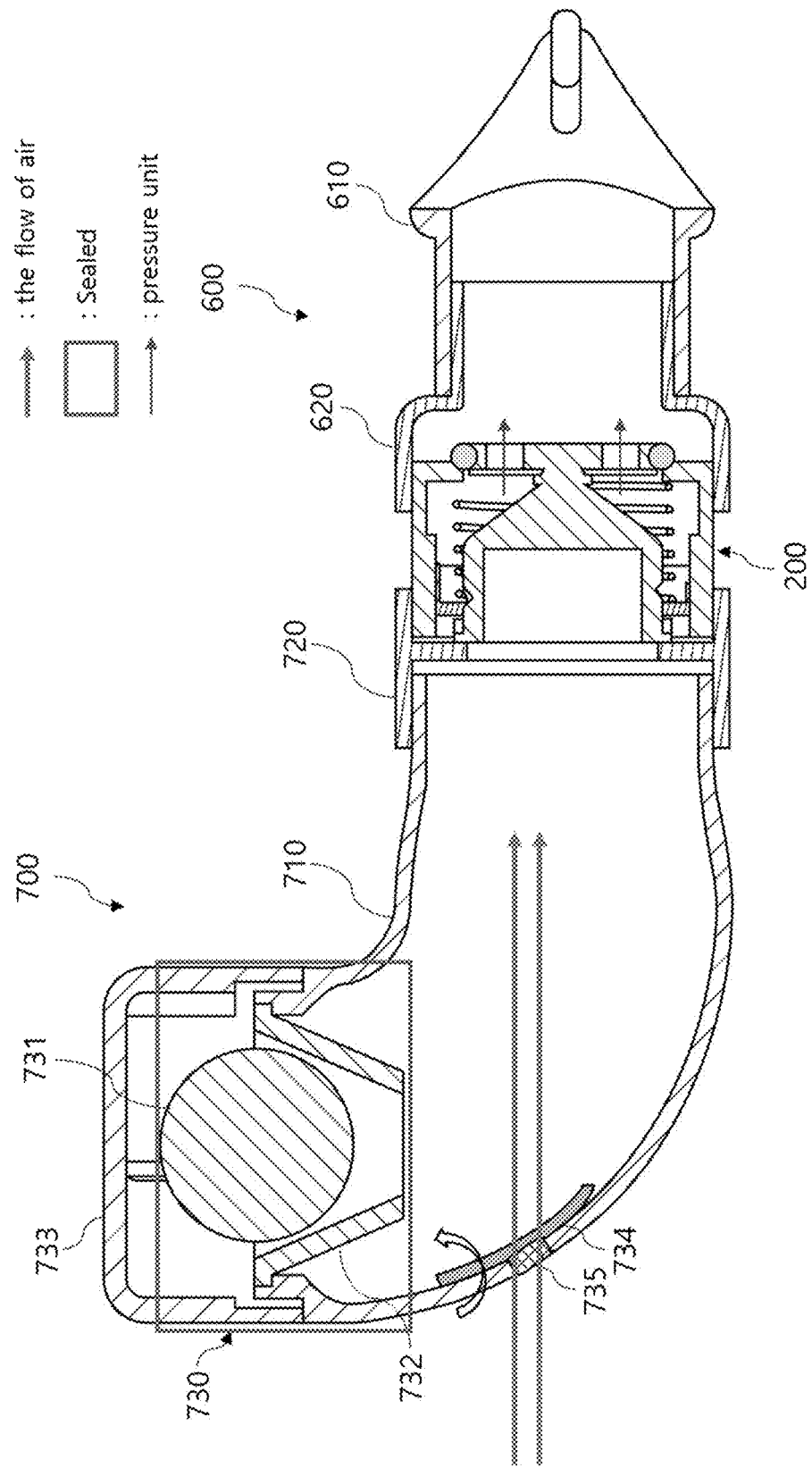
FIG. 29 is a cross-sectional view illustrating the state in which the pressure unit is disposed between the mouthpiece unit and the chest wall vibration unit of the respiratory muscle strengthening device according to the another embodiment of the present invention when a user performs inhalation.
Figure 30:
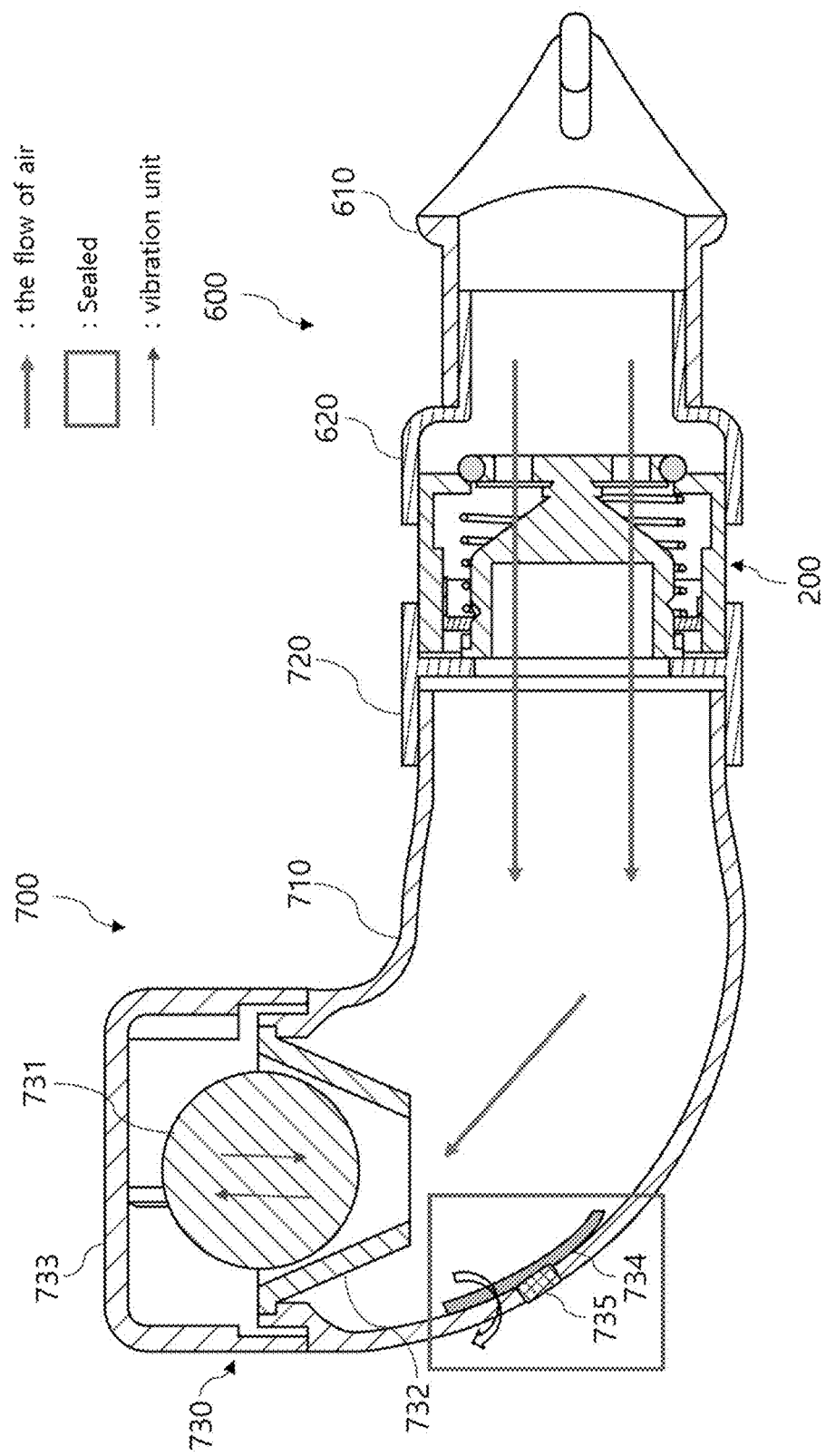
FIG. 30 is a cross-sectional view illustrating the state in which the pressure unit is disposed between the mouthpiece unit and the chest wall vibration unit of the respiratory muscle strengthening device according to the another embodiment of the present invention when a user performs exhalation.

More specifically, referring to FIGS. 28 to 30, the mouthpiece unit 600 includes a mouthpiece body 610 inserted into the mouth of the user, and a mouthpiece connector 620 coupled to an end of the mouthpiece body 610. One end of the mouthpiece connector 620 is coupled to the mouthpiece body 610, and the other end of the mouthpiece connector 620 surrounds at least a portion of the pressure unit 200 to fix the pressure unit 200.

Additionally, the chest wall vibration unit 700 includes a chest wall vibration unit body 710 formed in a hollow shape, a chest wall vibration unit connector 720 provided at one end of the chest wall vibration unit body 710 to fix the pressure unit 200 by surrounding at least a portion of the pressure unit 200, and a vibration generator 730 provided at the other end of the chest wall vibration unit body 710. Here, the vibration generator 730 includes a vibrator 731 vibrating vertically at the time of the user's exhalation, a vibrator support 732 provided below the vibrator 731 to prevent the vibrator 731 from escaping downward, a cap 733 provided at an upper portion of the vibrator 731 to prevent the vibrator 731 from escaping upward and having an outlet for discharging exhaled air of the user, and a silicone 734 provided inside the chest wall vibrator body 710. In addition, the chest wall vibration unit body 710 is provided with a communication hole 735 communicating with the outside, and the silicone 734 is made of an elastic material and usually serves to seal the communication hole 735. That is, the silicon 734 is bent to open the communication hole 735 when the user inhales air, but gets in contact with the chest wall vibration unit body 710 to close the communication hole 735 when the user exhales air.

In addition, one end of the chest wall vibration unit body 710 is coupled to the chest wall vibration unit connector 720, and the other end of the chest wall vibration unit body 710 is bent upward. That is, the vibrator 731 is supported not to escape downward by the vibrator support 732. Referring to FIG. 29, at the time of inhalation, air inside the chest wall vibration unit body 710 flows into the mouth of the user, and the pressure unit 200 acts to perform the respiratory motion. In this instance, the outside air does not flow into the chest wall vibration unit body 710 through the cap 733 by the vibration unit 731, but is in a sealed state. Referring to FIG. 30, at the time of exhalation, the vibrator 731 vibrates vertically to discharge exhaled air to the outside through the cap 733. In the above process, sputum is discharged by chest wall vibration by the vibration of the vibrator 731. Unlike a conventional respiratory rehabilitation device, such as the chest wall vibration unit 700, in a case in which the pressure unit 200 is applied, it is possible to easily carry the respiratory muscle strengthening device since being lightweight and compact-sized and being reduced in volume.

Figure 31:
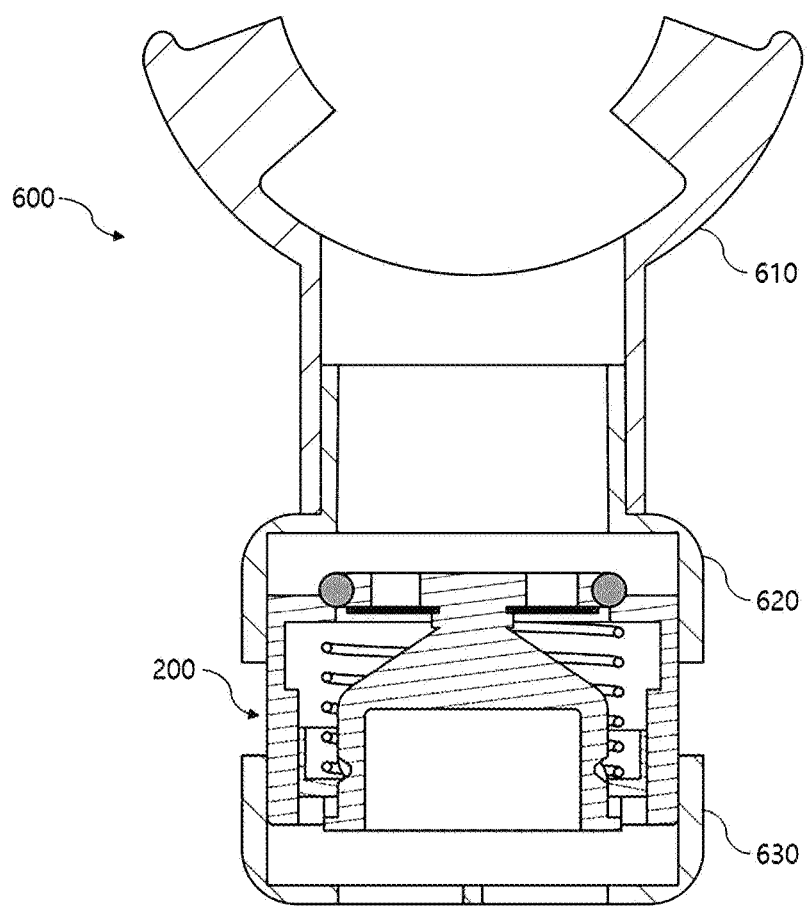
FIG. 31 is a view illustrating a state in which the mouthpiece unit and the pressure unit of the respiratory muscle strengthening device according to another embodiment of the present invention are coupled with each other.

Referring to FIG. 31, the mouthpiece unit 600 further includes a pressure unit cap 630 formed to surround at least a portion of the outer circumferential surface of the pressure unit 200. Here, one end of the pressure unit 200 is coupled to the mouthpiece connector 620, and the other end portion of the pressure unit 200 is coupled to the pressure unit cap 640. In this instance, the pressure unit cap 630 is rotatably coupled, and rotates the pressure unit cap 630 to adjust pressure while rotating. As a result, the user can perform the inhalation motion just by coupling the mouthpiece portion 600 and the pressure unit 200 to each other so as to be easily carried.

Figure 32:
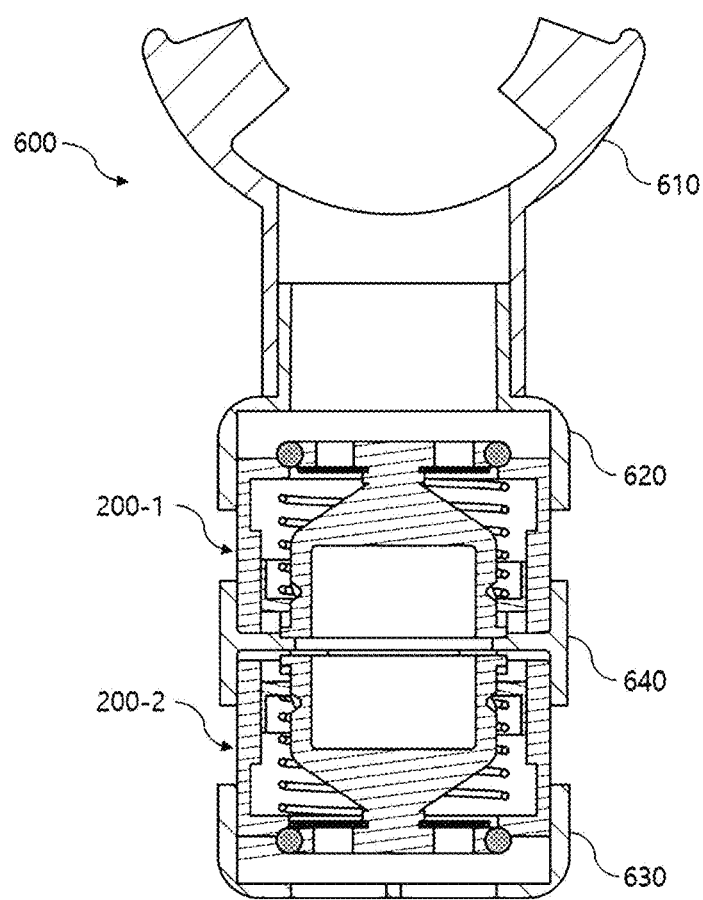
FIG. 32 is a view illustrating a state in which the mouthpiece unit and two pressure units of the respiratory muscle strengthening device according to another embodiment of the present invention are coupled with each other.

Referring to FIG. 32, the mouthpiece unit 600 further includes a pressure unit connector 640 formed to surround at least a portion of the outer circumferential surface of the pressure unit 200. That is, one end of the pressure unit connector 640 is coupled to a pressure unit 200-1, and the other end of the pressure unit connector 640 is coupled to another pressure unit 200-2. Here, two pressure units 200 are coupled to the mouthpiece unit 600 in a direction opposed to each other. That is, the two pressure units 200 are disposed to be axisymmetric on the basis of a central axis in the longitudinal direction of the pressure unit connector 640. In this instance, the pressure unit connector 640 is rotatably coupled, and makes the adjustment cover 220 rotate to adjust pressure when the pressure unit cap 640 is rotated. As a result, the user can perform the inhalation motion and the exhalation motion just by coupling the mouthpiece portion 600 and the two pressure units 200 to each other so as to be easily carried.

Figure 33:
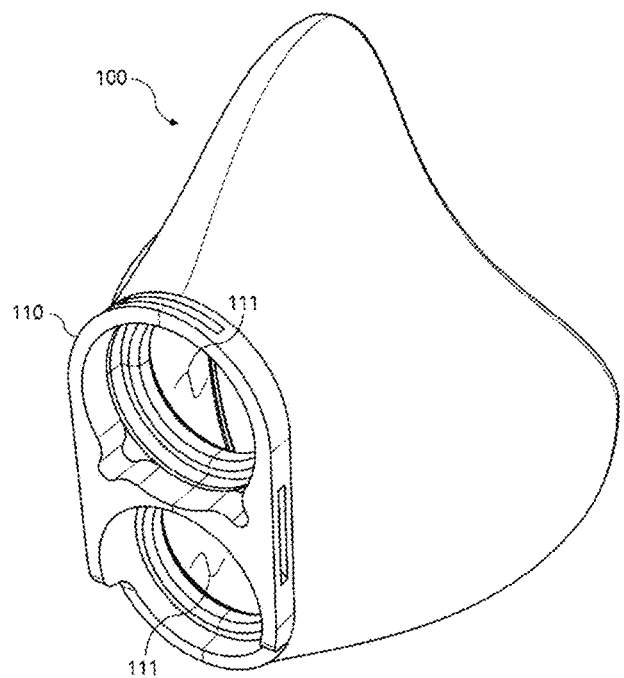
FIG. 33 is a view illustrating a state in which two pressure unit holes are formed so that the two pressure units can be coupled to a mask body.

Referring to FIG. 33, the mask body 100 includes two pressure unit holes 111 so that the two pressure units 200 can be coupled to the mask body 100. Here, the mask body 100 is formed integrally with the fixing portion 110, and the two pressure unit holes 111 of the mask body 100 are respectively disposed adjacent to the nose and the mouth of the user.

Figure 34:
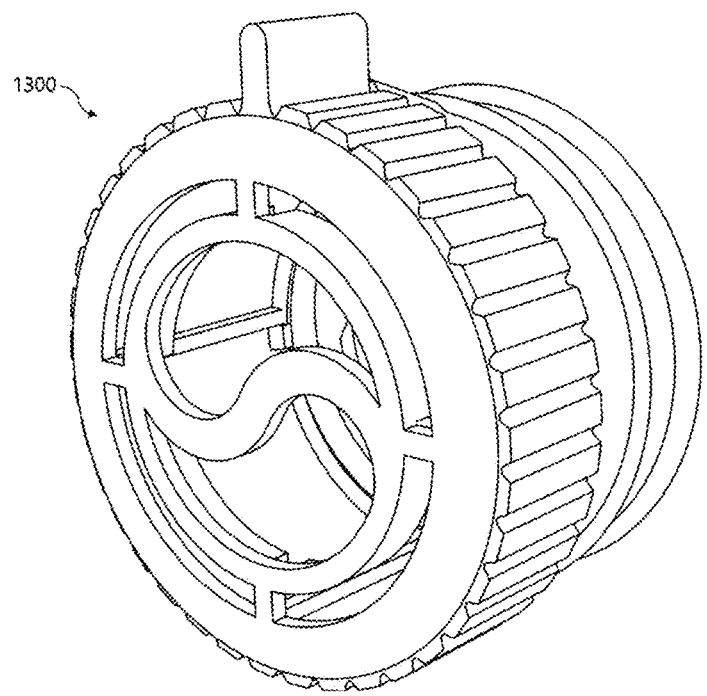
FIGS. 34 and 35 are views illustrating an inhalation blocking unit of a respiratory muscle strengthening device according to another embodiment of the present invention.
Figure 35:
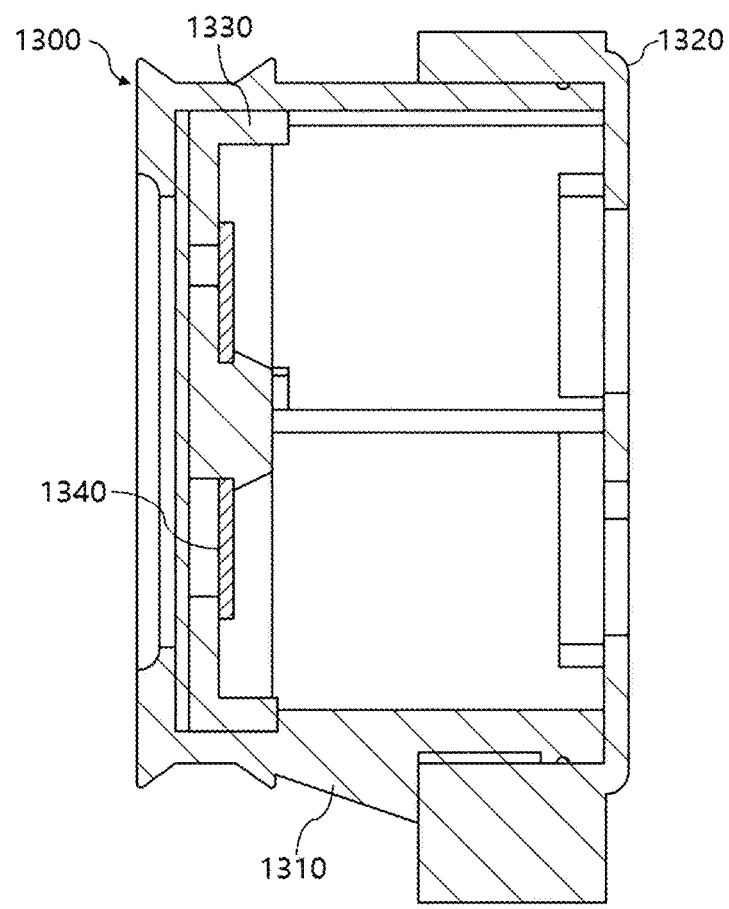

Referring to FIGS. 34 and 35, the pressure unit 1300 further includes an inhalation blocking portion 1330 and a silicon film 1340. In this instance, the inhalation blocking portion 1330 and the silicon film 1340 are in close contact with the frame part 1310 to serve as sealing by interfering with the flow of a fluid when the user inhales air. In addition, the silicon film 1340 is bent to be spaced apart from the frame unit 1310 to discharge the user's exhaled air to the outside when the user exhales.

Figure 36:
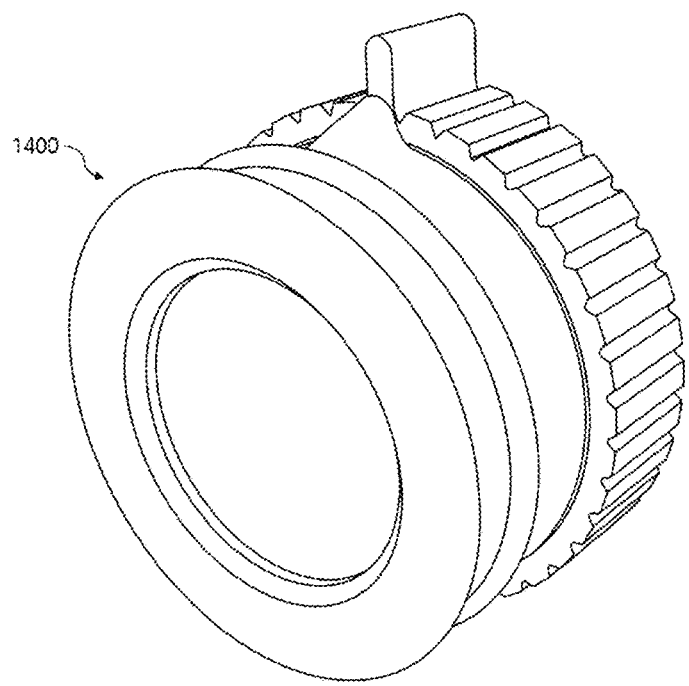
FIGS. 36 and 37 are views illustrating a state in which a regulator of the respiratory muscle strengthening device according to the another embodiment of the present invention is provided in the opposite direction and a filter is fixed.
Figure 37:
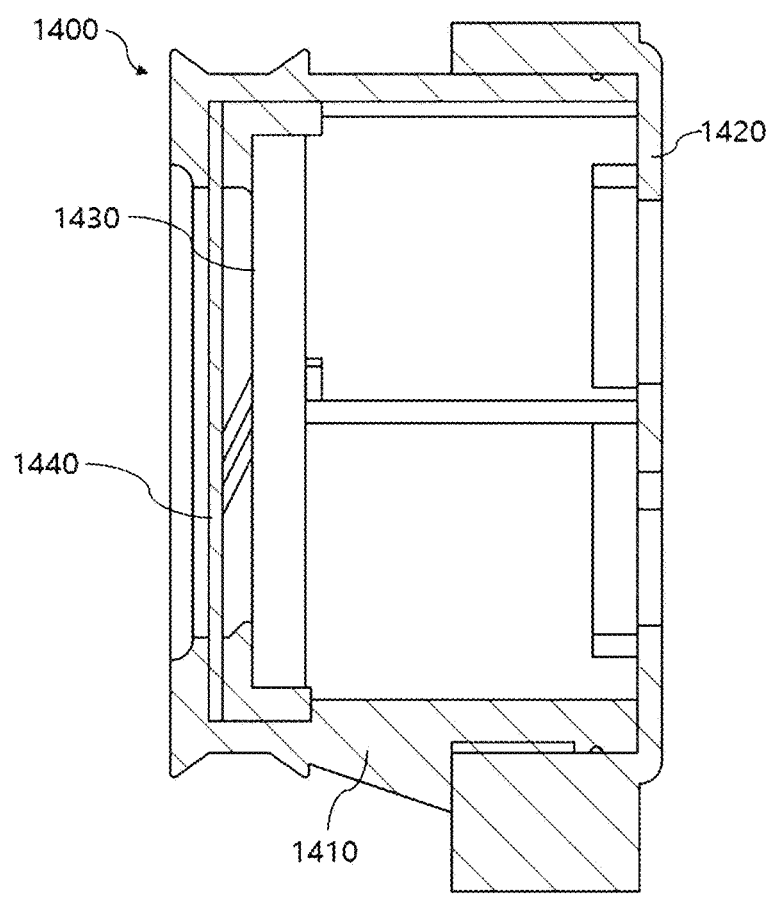

Referring to FIGS. 36 and 37, compared with the pressure unit 200, the pressure unit 1400 has the regulator 1430 spaced apart from the adjustment cover 1420 so as to fix the filter 1440. That is, the filter 1440 is disposed inside the pressure unit 1400 so as to be selectively assembled if necessary.

Figure 38:
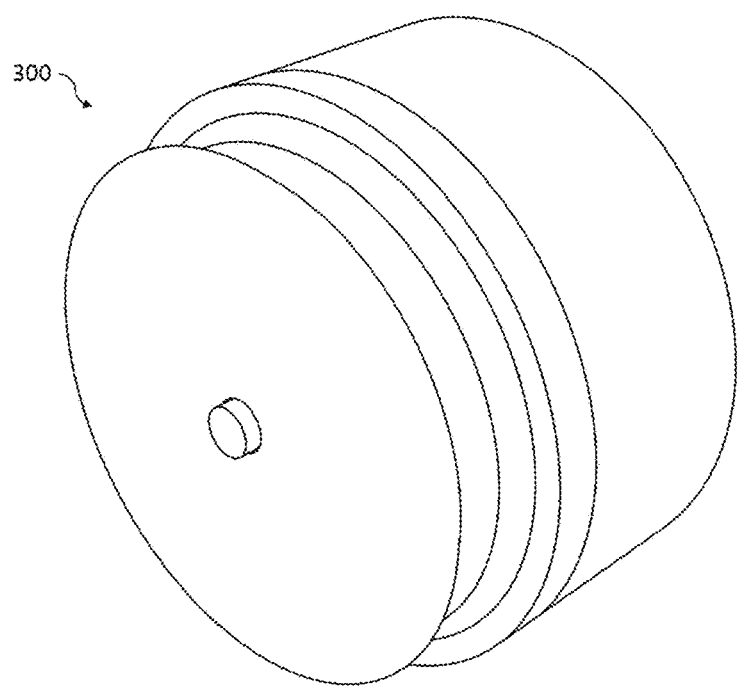
FIGS. 38 and 39 are views illustrating a sensor unit of a respiratory muscle strengthening device according to an embodiment of the present invention.
Figure 39:
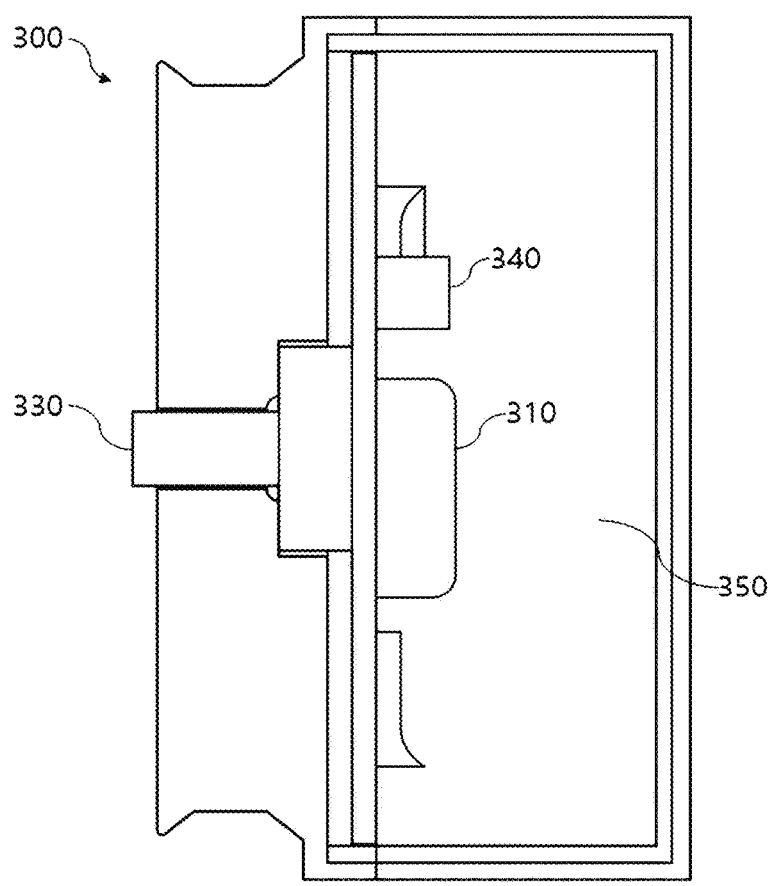

Referring to FIGS. 38 and 39, the sensor unit 300 further includes a sensing portion 330, an integrated circuit 340, and a housing 350, and transmits the respiration pattern of the user to an application.

As a result, the respiratory muscle strengthening device according to the present invention can protect respiratory organs of a user even when the user does outdoor exercise such as jogging, riding, etc. as well as indoor exercise, and allow the user to do exercise such as jogging, riding, etc. together with respiratory motion, thereby improving efficiency of exercise. In addition, the respiratory muscle strengthening device according to the present invention enables the user to perform respiratory muscle strengthening exercise through pressure during inhalation by coupling the pressure unit 200 between the mouthpiece unit 600 and the chest wall vibration unit 700 and to discharge sputum through chest wall vibration during exhalation.

As described above, the foregoing description of the present disclosure has been presented for the purposes of illustration and description. It is apparent to a person having ordinary skill in the art to which the present disclosure relates that the present disclosure can be easily modified into other detailed forms without changing the technical principle or essential features of the present disclosure.

Therefore, the foregoing embodiments should be regarded as illustrative rather than limiting in all aspects. While the present disclosure has been shown and described with reference to various embodiments thereof, it will be understood by those skilled in the art that various changes in form and details may be made therein without departing from the spirit and scope of the present disclosure as defined by the appended claims and their equivalents.

EXPLANATION OF REFERENCE NUMERALS

100: mask body
110: fixing portion
111: pressure unit hole
112: sensor unit hole
120: coupling groove
130: packing
200: pressure unit
210: frame part
211: rail portion
212: adjustment protrusion
220: adjustment cover
221: elastic protrusion
222: insertion groove
223: cover rib
230: main filler
231: insertion protrusion
232: shaft
233: main filler rib
240: sub-filler
241: through hole
242: sealing groove
243: sub-filler rib
250: regulator
251: rail groove
252: interference portion
260: spring
270: shield
271: insertion hole
280: sealing member
300: sensor unit
310: communication unit
320: application
330: sensing portion
340: integrated circuit
350: housing
400: band unit
410: ear loop portion
420: extension portion
421: buckle
422: Velcro
500: cover unit
510: filtering portion
1200: pressure unit
1210: body
1220: cover
1230: filler
1240: regulator
1250: spring
1260: disk frame
1270: silicon
1300: pressure unit
1310: frame part
1320: cover
1330: inhalation blocking portion
1340: silicon film
1400: pressure unit
1410: frame part
1420: adjustment cover
1430: regulator
1440: adjustment cover
2300: sensor unit
600: mouthpiece unit
610: mouthpiece body
620: mouthpiece connector
630: pressure unit cap
640: pressure unit connector
700: chest wall vibration unit
710: chest wall vibration unit body
720: chest wall vibration unit connector
730: vibration generator
731: vibrator
732: vibrator support
733: cap
734: silicon
735: communication hole

The invention claimed is:

1. A respiratory muscle strengthening device comprising:
a mouthpiece unit;
a pressure unit of which one end is coupled to the mouthpiece unit to control air inhaled from outside; and
a chest wall vibration unit coupled to another end of the pressure unit,
wherein the mouthpiece unit comprises:
a mouthpiece body configured to be inserted into the mouth of a user; and
a mouthpiece connector of which one end is coupled to an end of the mouthpiece body and another end surrounds at least a portion of the pressure unit to fix the pressure unit,
wherein the chest wall vibration unit comprises:
a chest wall vibration unit body formed in a hollow shape and having a communication hole communicating with the outside;

a chest wall vibration unit connector provided at one end of the chest wall vibration unit body to fix the pressure unit by surrounding at least a portion of the pressure unit; and a vibration generator provided at another end of the chest wall vibration unit body, and wherein the vibration generator comprises:

a vibrator vibrating vertically at the time of the user's exhalation;

a vibrator support provided below the vibrator to prevent the vibrator from escaping downward;

a cap provided at an upper portion of the vibrator to prevent the vibrator from escaping upward and having an outlet for discharging exhaled air of the user; and a silicone provided inside the chest wall vibrator body to open the communication hole when the user inhales air and to close the communication hole when the user exhales air.

* * * * *